United States Patent
Schweinsberg et al.

(10) Patent No.: US 8,790,417 B2
(45) Date of Patent: Jul. 29, 2014

(54) GENTLE HAIR COLOR PRETREATMENT WITH SILICONE AND OILY OXIDANTS

(71) Applicant: Henkel AG & Co. KGaA, Duesseldorf (DE)

(72) Inventors: Matthias Schweinsberg, Hamburg (DE); Jisook Baek, Hamburg (DE); Astrid Kleen, Hamburg (DE); Erik Schulze zur Wiesche, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/132,155

(22) Filed: Dec. 18, 2013

(65) Prior Publication Data
US 2014/0165303 A1      Jun. 19, 2014

(30) Foreign Application Priority Data
Dec. 19, 2012   (DE) .......................... 10 2012 223 809

(51) Int. Cl.
| | |
|---|---|
| *A61Q 5/10* | (2006.01) |
| *A61Q 5/00* | (2006.01) |
| *A61K 8/25* | (2006.01) |
| *A61K 8/898* | (2006.01) |
| *A61K 8/92* | (2006.01) |

(52) U.S. Cl.
CPC ... *A61Q 5/10* (2013.01); *A61K 8/25* (2013.01); *A61K 8/898* (2013.01); *A61K 8/92* (2013.01)
USPC ....................... 8/405; 8/406; 8/581; 424/70.1

(58) Field of Classification Search
CPC ............. A61Q 5/00; A61Q 5/10; A61K 8/25; A61K 8/898
USPC ............................ 8/405, 406, 581; 424/70.1
See application file for complete search history.

(56) References Cited

U.S. PATENT DOCUMENTS

| | | | |
|---|---|---|---|
| 6,824,764 B2 * | 11/2004 | Devin-Baudoin et al. ... | 424/70.1 |
| 7,220,408 B2 | 5/2007 | Decoster et al. | |
| 7,223,385 B2 | 5/2007 | Gawtrey et al. | |
| 7,485,289 B2 | 2/2009 | Gawtrey et al. | |
| 7,504,094 B2 | 3/2009 | Decoster et al. | |

FOREIGN PATENT DOCUMENTS

| | | |
|---|---|---|
| AU | 2005256329 B2 | 1/2006 |
| DE | 19756454 C1 | 6/1999 |

OTHER PUBLICATIONS

STIC Search Report dated Feb. 10, 2014.*

* cited by examiner

*Primary Examiner* — Eisa Elhilo
(74) *Attorney, Agent, or Firm* — David K. Benson

(57) ABSTRACT

Methods and compounds are provided for oxidative coloring of keratinic fibers, in particular hair. The method includes applying a pretreatment agent onto the hair, where the pretreatment agent includes at least one 4-morpholinomethyl-substituted silicone. A hair coloring agent is applied to the hair subsequent to the pretreatment agent within a time span from about 1 second to about 24 hours. The hair coloring agent is obtained by mixing a composition (A), which contains at least one oxidation dye precursor of the developer type and at least one oxidation dye precursor of the coupler type, with a composition (B) that contains at least one oxidizing agent. Composition (B) contains at least one cosmetic oil in a total quantity from 10 to 80 wt %, based on the weight of composition (B).

15 Claims, No Drawings

GENTLE HAIR COLOR PRETREATMENT WITH SILICONE AND OILY OXIDANTS

CROSS REFERENCE TO RELATED APPLICATION

This application claims priority to German Patent Application Number DE 10 2012 223 809.3, filed on Dec. 19, 2012.

TECHNICAL FIELD

The present invention relates to a low-impact method for oxidative hair coloring in which keratinic fibers are protected from oxidizing influences.

BACKGROUND

In the context of oxidative coloring of hair, the problem arises that irritation of the scalp and damage to the keratinic fibers can occur as a result of the aggressive agents. In particular, the natural hydrophobicity of the keratinic fibers is reduced because the coloring agents resp. lightening agents must first make the hair capable of penetration in order to exert their effect. The water-repellent effect on the one hand, however, provides natural protection for the hair; on the other hand, parameters desired by the consumer, such as shine, softness, suppleness, and the "drape" of the hair, are closely linked to it.

In order to overcome the aforesaid disadvantages, so-called pretreatment agents that are intended to protect the hair from aggressive influence are on the market. These often make the hair heavy, however, or negatively affect the outcome of the lightening resp. coloring of the hair that takes place subsequently; in particular, the washing fastness of the color can be degraded by the pretreatment agent.

The object of the present invention was to make available a method for oxidative hair coloring, with a hair-protecting pretreatment, that overcomes the aforesaid disadvantages without counteracting the success of a subsequent oxidative coloring treatment. The intention was in particular to make available a method in which the hair is not made heavier, and in which the desired effect can also be achieved in the context of a pretreatment not occurring immediately prior to the oxidative coloring treatment, with the result that the time span between pretreatment and coloring can be extended.

The use of aminated silicones in hair care is established art. They are widely used in shampoos and in particular in conditioners in order to exert care-providing effects therein. EP 1771144 B1, for example, discloses hair-conditioning agents having aminofunctional silicones. The agents described therein are post-treatment agents.

European patents EP 1312334 B1 (aminosilicone and thickener) and EP 1312335 B1 (aminosilicone and conditioner) also disclose hair post-treatment agents. Extremely water-rich formulations are also disclosed in the former document.

BRIEF SUMMARY

A method is provided for oxidative coloring of keratinic fibers, in particular hair. The method includes applying a pretreatment agent onto the hair, where the pretreatment agent includes at least one 4-morpholinomethyl-substituted silicone. A hair coloring agent is applied to the hair subsequent to the pretreatment agent within a time span from about 1 second to about 24 hours. The hair coloring agent is obtained by mixing a composition (A), which contains at least one oxidation dye precursor of the developer type and at least one oxidation dye precursor of the coupler type, with a composition (B) that contains at least one oxidizing agent. Composition (B) contains at least one cosmetic oil in a total quantity from 10 to 80 wt %, based on the weight of composition (B).

DETAILED DESCRIPTION

It has now been found that a pretreatment of the keratinic fibers with special 4-morpholinomethyl-substituted silicones within a specific time period prior to an oxidative coloring treatment not only results in appreciably improved hair protection but also produces particularly good coloring results, in particular colors having a high level of fastness, without negatively affecting the outcome of the oxidative coloring treatment. "Hair protection" is to be understood for purposes of this Application in particular to mean that the structure of the keratinic fibers, in particular of the hair, is less intensely attacked by the oxidizing agent, so that the surface of the fibers resp. of the hair becomes less roughened, the hair ends experience less splitting, and/or less hair breakage occurs.

The subject matter of the present invention is, in a first embodiment, a method for oxidative coloring of keratinic fibers, in particular of hair, in which a) a pretreatment agent that contains at least one 4-morpholinomethyl-substituted silicone of formula (V),

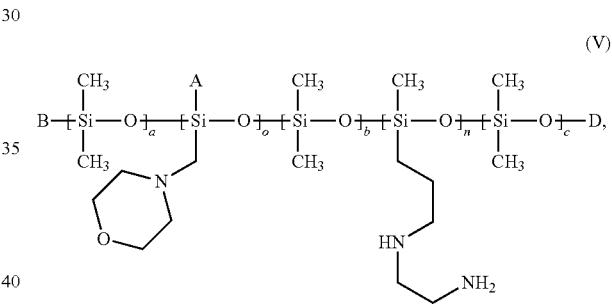

in which

A denotes a structural unit (I), (II), or (III) bound via —O—

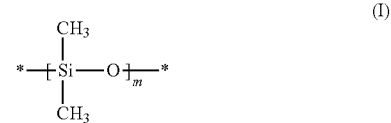

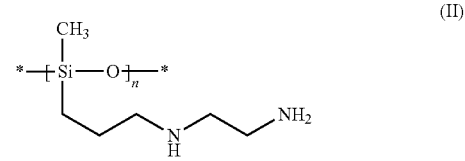

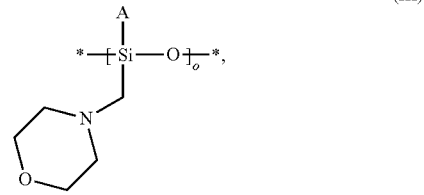

or an oligomeric or polymeric residue bound via —O— containing structural units of formulas (I), (II), or (III), or half of an oxygen connecting atom to a structural unit (III), or denotes —OH,

* denotes a bond to one of the structural units (I), (II), or (III), or denotes a terminal group B (Si-bound) or D (O-bound), B denotes an —OH, —O—Si(CH₃)₃, —O—Si(CH₃)₂OH, —O—Si(CH₃)₂OCH₃ group, D denotes an —H, —Si(CH₃)₃, —Si(CH₃)₂OH, —Si(CH₃)₂OCH₃ group, a, b, and c denote integers from 0 to 990, with the provision that a+b+c>0, m, n, and o denote integers from 2 to 990, is applied onto the keratinic fibers, in particular onto the hair, b) subsequently, within a time span from one about second to about 24 hours after step a), a hair coloring agent is applied onto the keratinic fibers, where the hair coloring agent is obtained by mixing a composition (A), which contains at least one oxidation dye precursor of the developer type and at least one oxidation dye precursor of the coupler type, with a composition (B) that contains at least one oxidizing agent, where composition (B) contains at least one cosmetic oil in a total quantity from about 10 to about 80 wt %, based on the weight of composition (B).

Pretreatment agents preferably used according to the present invention are characterized in that they contain the at least one 4-morpholinomethyl-substituted silicone of formula (V), which comprises respectively at least one of the structural units of formulas (I), (II), and (III), in a total quantity from about 0.001 to about 5 wt %, preferably about 0.005 to about 2 wt %, particularly preferably about 0.01 to about 1 wt %, extraordinarily preferably about 0.02 to about 0.1 wt %, based in each case on the total weight of the pretreatment agent.

Pretreatment agents preferably used according to the present invention are characterized in that they contain the at least one 4-morpholinomethyl-substituted silicone of formula (V) in a form emulsified in water. Pretreatment agents used particularly preferably contain about 30 to about 98 wt %, preferably about 40 to about 90 wt %, particularly preferably about 50 to about 85 wt %, extraordinarily preferably about 60 to about 80 wt % water, based in each case on the total weight of the pretreatment agent.

Pretreatment agents used particularly preferably are present in the form of an oil-in-water emulsion in which the number-average size of the silicone particles in the emulsion is in the range from about 3 to about 500 nanometers (nm), preferably in the range from about 5 to about 60 nm.

Structural units of formulas (I), (II), and (III) can be present statistically distributed in the molecule, but the silicones used according to the present invention can also be block copolymers made up of blocks of the individual structural units, in which context the blocks can in turn be present in statistically distributed fashion.

The * on the free valences of structural units (I), (II), or (III) denotes a bond to one of the structural units (I), (II), or (III) or a terminal group B (Si-bound) or D (O-bound).

The silicones used according to the present invention can be trimethylsilyl-terminated at both ends (D=—Si(CH₃)₃, B=—O—Si(CH₃)₃), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which B=—O—Si(CH₃)₂OH and D=—Si(CH₃)₃
B=—O—Si(CH₃)₂OH and D=—Si(CH₃)₂OH
B=—O—Si(CH₃)₂OH and D=—Si(CH₃)₂OCH₃
B=—O—Si(CH₃)₃ and D=—Si(CH₃)₂OH
B=—O—Si(CH₃)₂OCH₃ and D=—Si(CH₃)₂OH.

These silicones result in exorbitant improvements in the hair properties of the hair treated in accordance with the method according to the present invention, in particular in a tremendous decrease in contact angle.

In structural unit (III), residue A can denote
a structural unit (I), (II), or (III) bound via —O—, or
an oligomeric or polymeric residue bound via —O— containing structural units of formulas (I), (II), and (III), or
half of an oxygen atom connecting to a structural unit (III), or can denote —OH.

In the first case, structural unit (III) becomes one of the structural units (IIIa), (IIIb), or (IIIc):

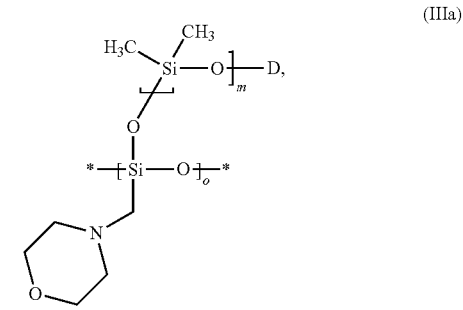

(IIIa)

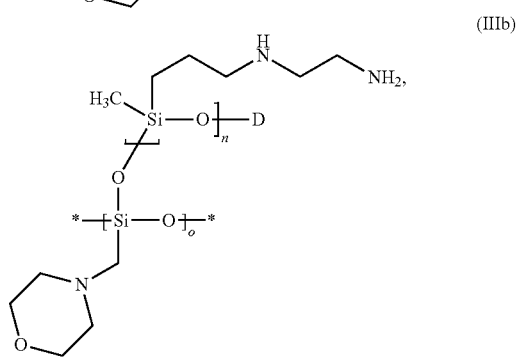

(IIIb)

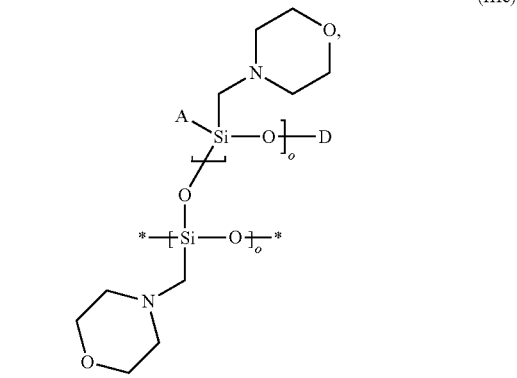

(IIIc)

where m=n=o=1, and A resp. D are as defined above.

In the second case, in the formulas (IIIa), (IIIb), and (IIIc) recited above the indices m, n, and o can denote integers from 2 to 990. The second case also, however, covers oligomeric or polymeric residues that contain at least two different structural units of formulas (I), (II), or (III), as depicted in formula (IIId):

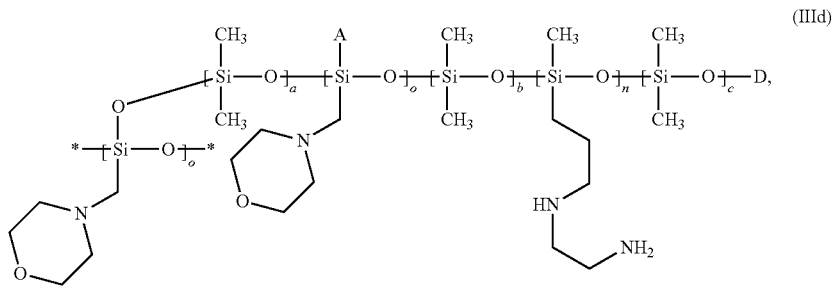
(IIId)

in which a, b, and c denote integers from 0 to 990, with the provision that a+b+c>0, and n and o denote integers from 1 to 990.

In the third case, A denotes half of an oxygen atom connecting to a structural unit (III) (depicted in structural unit (IIIe)) or denotes —OH (depicted in structural unit (IIIf))

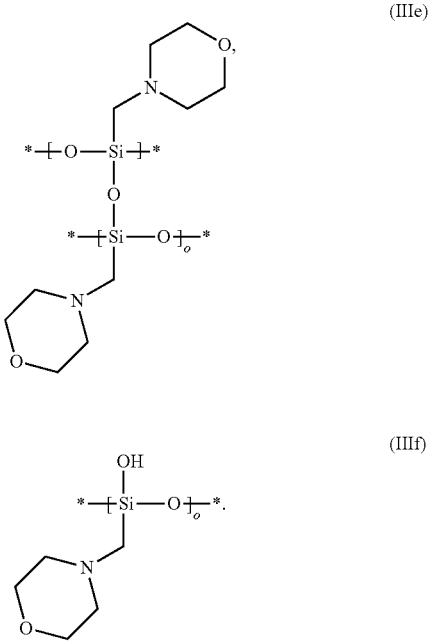

As already mentioned, the structural units of formulas (I), (II), and (III) can preferably be present in statistically distributed fashion. Pretreatment agents preferably used according to the present invention contain at least one 4-morpholinomethyl-substituted silicone of formula (V)

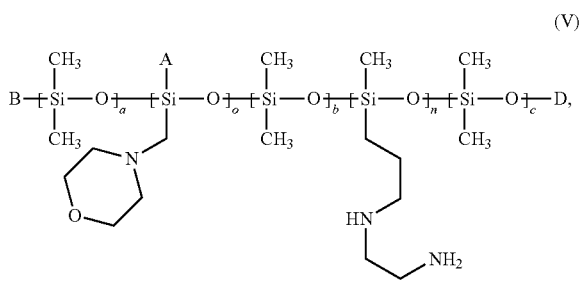

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, n, and o denote integers from 1 to 990.

Structural formula (V) is intended to illustrate the fact that the siloxane groups n and o do not obligatorily need to be bound directly to an end grouping B resp. D. Instead, in preferred formulas (V) a>0 or b>0, and in particularly preferred formulas (V) a>0 and b>0, i.e. the terminal grouping B resp. D is preferably bound to a dimethylsiloxy grouping. In formula (V) as well, the siloxane units a, b, c, n, and o are preferably statistically distributed.

The silicones represented by formula (V) and used according to the present invention can also be trimethylsilyl-terminated at both ends (D=—Si(CH$_3$)$_3$, B=—O—Si(CH$_3$)$_3$), but they can also be dimethylsilylhydroxy- or dimethylsilylmethoxy-terminated at one or two ends. Silicones used particularly preferably in the context of the present invention have at least one terminal dimethylsilylhydroxy group, i.e. are selected from silicones in which B=—O—Si(CH$_3$)$_2$OH and D=—Si(CH$_3$)$_3$ B=—O—Si(CH$_3$)$_2$OH and D=—Si(CH$_3$)$_2$OH B=—O—Si(CH$_3$)$_2$OH and D=—Si(CH$_3$)$_2$OCH$_3$ B=—O—Si(CH$_3$)$_3$ and D=—Si(CH$_3$)$_2$OH B=—O—Si(CH$_3$)$_2$OCH$_3$ and D=—Si(CH$_3$)$_2$OH.

These 4-morpholinomethyl-substituted silicones of formulas (V), which respectively comprise at least one of the structural units of formula (I), (II), and (III), result in surprisingly large improvements in the hair properties of the hair treated in accordance with the method according to the present invention, in particular in tremendously improved hair protection and color protection in the context of oxidative hair coloring.

In formula (V) as well, residue A can denote a structural unit (I), (II), or (III) bound via —O—, or an oligomeric or polymeric residue bound via —O— containing structural units of formulas (I), (II), and (III), or half of an oxygen atom connecting to a structural unit (III), or can denote —OH.

By analogy with the statements regarding structural unit (III), formula (V) is thus refined to one of formulas (Va), (Vb), (Vc), (Vd), (Ve), or (Vf):

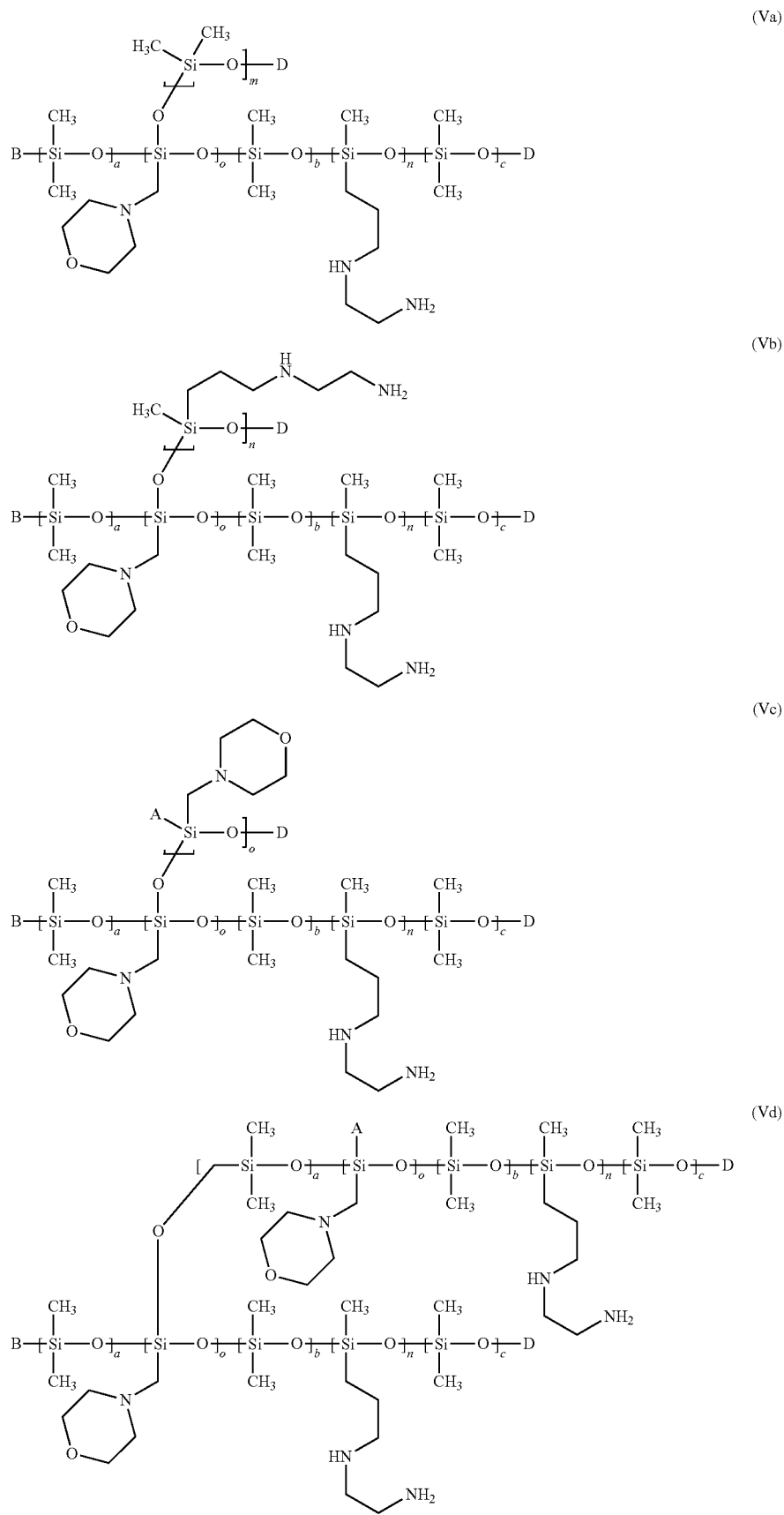

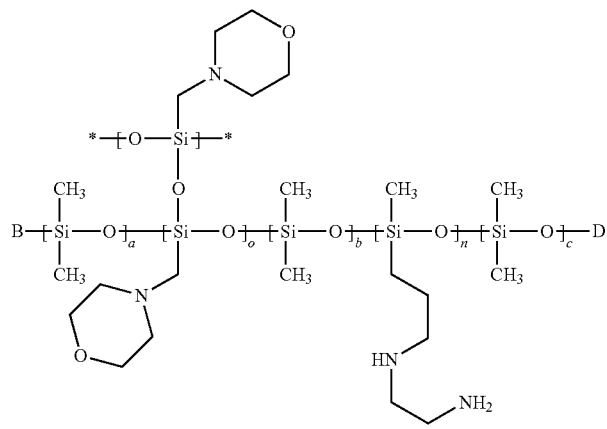

(Ve)

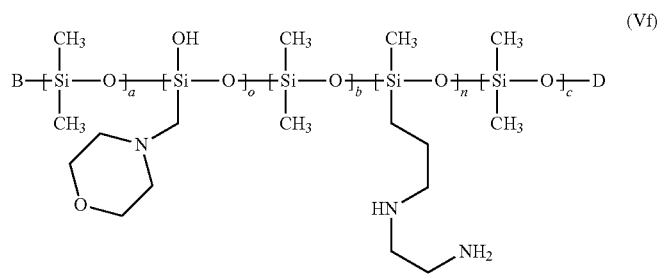

(Vf)

Structural unit (III) resp. the siloxane units o in formulas (V) can, via group A, constitute nest structures resp. partial cage structures when A denotes half of an oxygen atom connecting to a structural unit (III). Pretreatment agents according to the present invention that contain silicones having corresponding 4-morpholinomethyl-substituted silsesquioxane substructures are preferred according to the present invention, since these silicones result in enormously improved hair protection in the context of oxidative coloring treatment.

Pretreatment agents preferably used according to the present invention are characterized in that they contain at least one 4-morpholinomethyl-substituted silicone that comprises structural units of formula (VI)

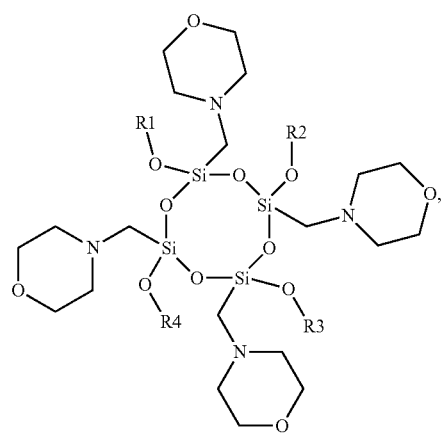

(VI)

in which

R1, R2, R3, and R4 mutually independently denote —H, —CH$_3$, a group D, a structural unit (I), (II), or (III), or an oligomeric or polymeric residue containing structural units of formulas (I), (II), or (III), or two of the residues R1, R2, R3, and R4 denote a structural unit —Si(R6)(R5)-, where R5=—CH$_3$ or a structural unit of formula (I) or (II) or (III) or an oligomeric or polymeric residue containing structural units of formulas (I), (II), or (III), R6=—OH, —CH$_3$, or a structural unit of formula (I) or (II) or (III) or an oligomeric or polymeric residue containing structural units of formulas (I), (II), or (III).

In preferred silicones of formula (VI), at least one of the residues R1, R2, R3, or R4 denotes an oligomeric or polymeric residue containing structural units of formulas (I), (II), or (III).

In further preferred silicones of formula (VI), at least one of the residues R1, R2, R3, or R4 denotes an oligomeric or polymeric residue containing structural units of formulas (I) and (II).

In even further preferred silicones of formula (VI), at least one of the residues R1, R2, R3, or R4 denotes an oligomeric or polymeric residue containing structural units of formulas (I) and (II) and (III).

At least one of the residues R1, R2, R3, or R4 preferably denotes an —[—Si(CH$_3$)$_2$—O]$_m$ grouping, i.e. an oligomer resp. polymer of structural unit (I). In addition, preferably structural unit (II) resp. an oligomer or polymer thereof is never bound in the molecule alone, but instead always in a statistical distribution with further structural units of formula (I) as one of the residues R1, R2, R3, or R4.

Preferred silicones of formula (VI) can be described by formula (VI a)

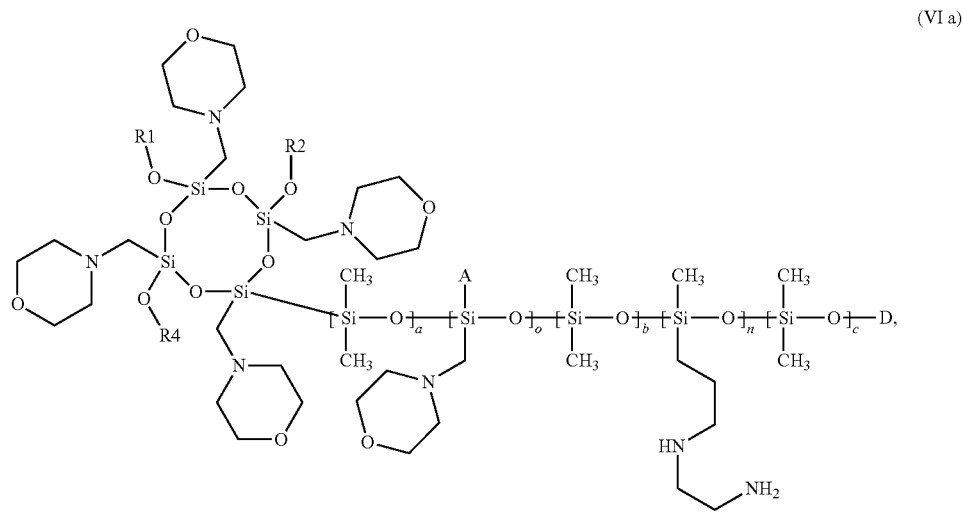

(VI a)

in which
R1, R2, and R4 mutually independently denote —H, —CH$_3$, a group D, a structural unit (I), (II), or (III), or an oligomeric or polymeric residue containing structural units of formulas (I), (II), or (III), or two of the residues R1, R2, and R4 denote a structural unit —Si(R6)(R5)-, where
  R5=—CH$_3$ or a structural unit of formula (I) or (II) or (III) or an oligomeric or polymeric residue containing structural units of formulas (I), (II), or (III),
  R6=—OH, —CH$_3$, or a structural unit of formula (I) or (II) or (III) or an oligomeric or polymeric residue containing structural units of formulas (I), (II), or (III), A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, n, and o denote integers from 1 to 990.

Further preferred silicones of formula (VI) can be described by formula (VI b)

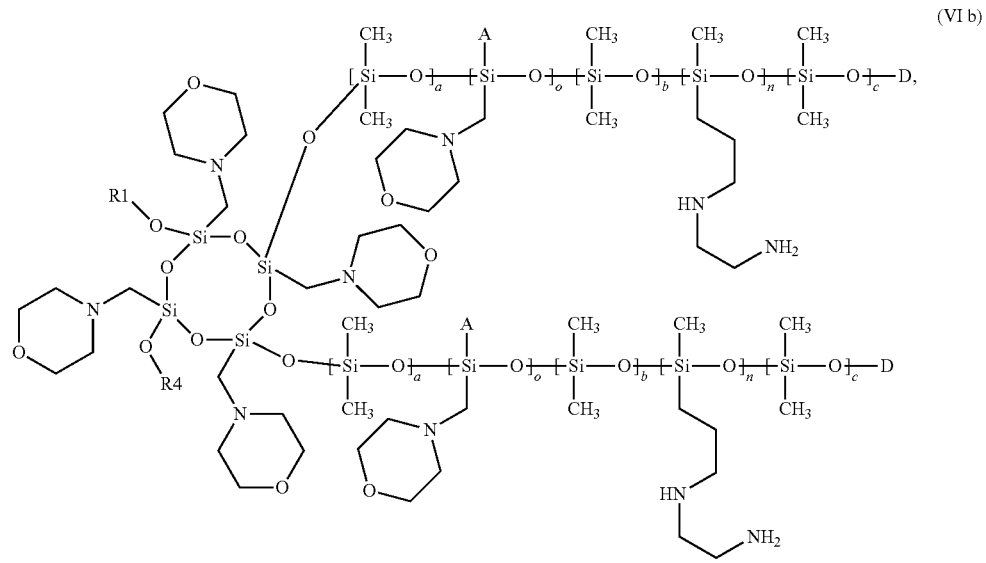

(VI b)

in which the residues and indices are as defined above.

Particularly preferred silicones of formula (VI) can be described by formula (VI c)

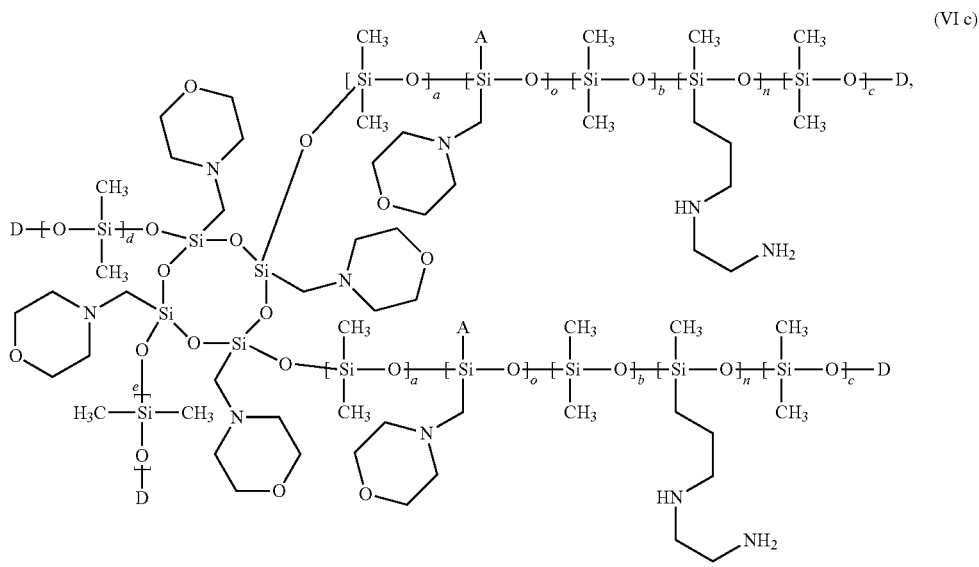

(VI c)

in which the residues and indices are as defined above, and the indices d and e denote integers from 0 to 990.

In formulas (VI a), (VI b), and (VI c), at least one of the groupings D preferably denotes —Si(CH$_3$)$_2$OH.

The silsesquioxane structures can be even more pronounced in the 4-morpholinomethyl-substituted silicones used according to the present invention, which intensifies the advantageous effects. Particularly preferred pretreatment agents used according to the present invention are characterized in that they contain at least one 4-morpholinomethyl-substituted silicone that comprises structural units of formula (VII)

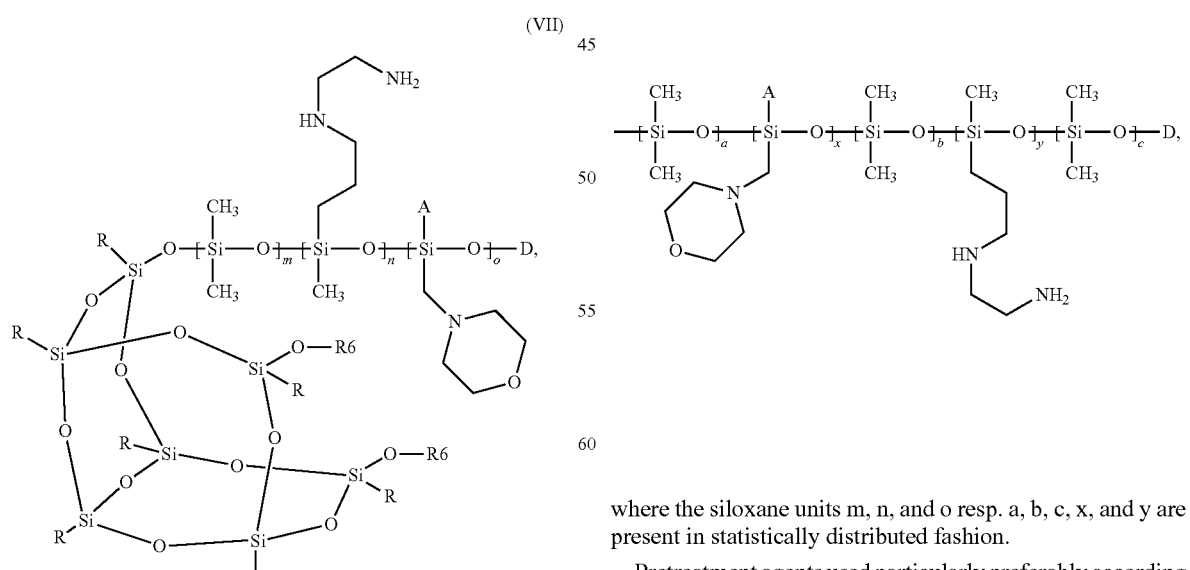

in which

A denotes a structural unit (I), (II), or (III) bound via —O—, or an oligomeric or polymeric residue bound via —O— containing structural units of formulas (I), (II), or (III), or half of an oxygen atom connecting to a structural unit (III), or denotes —OH, D denotes an —H, —Si(CH$_3$)$_3$, —Si(CH$_3$)$_2$OH, —Si(CH$_3$)$_2$OCH$_3$ group, R denotes a 4-morpholinomethyl residue, R6 denotes —H or the grouping where the siloxane units m, n, and o resp. a, b, c, x, and y are present in statistically distributed fashion.

Pretreatment agents used particularly preferably according to the present invention contain at least one silicone of the following formula (VII a)

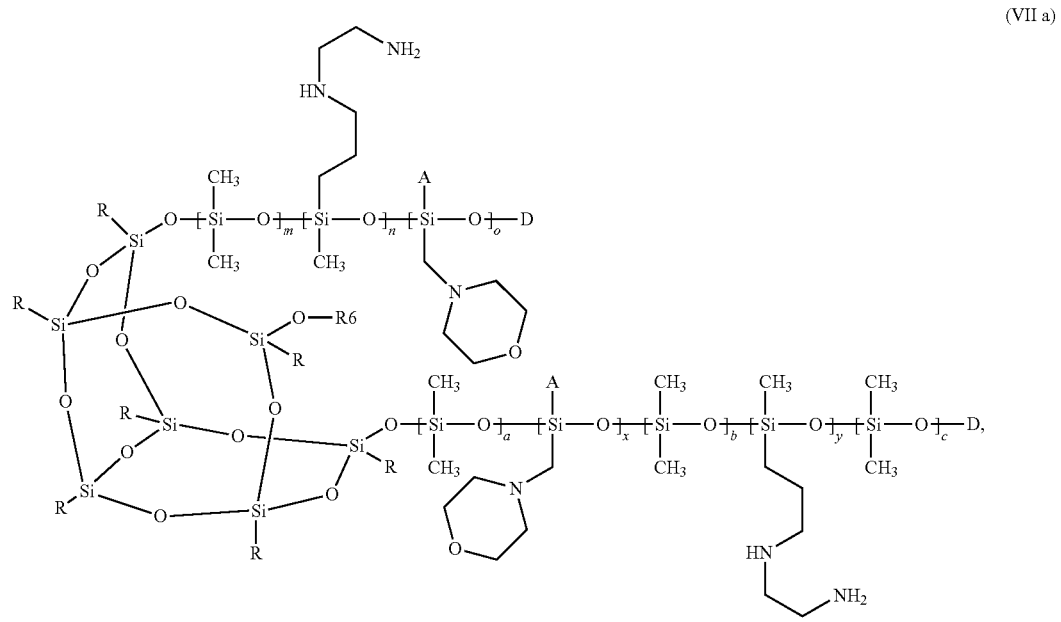

(VII a)

with the definitions as for formula (VII).

Very particularly preferred pretreatment agents used according to the present invention contain at least one silicone of the following formula (VII b)

In formulas (VII), (VII a), and (VII b), the bridging oxygen atoms between the morpholinomethyl-substituted silicon atoms can also be supplemented by an —[—Si(CH$_3$)$_2$—O]$_m$ grouping, i.e. an oligomer or polymer of structural unit (I).

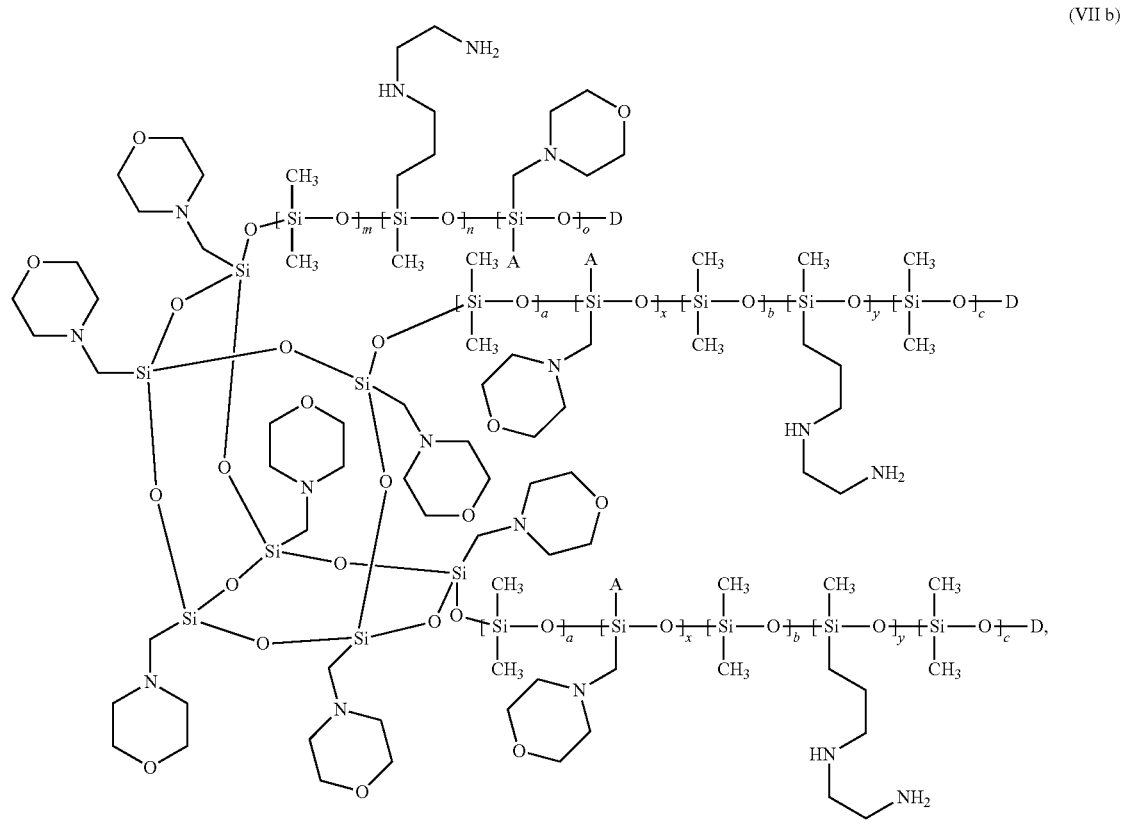

(VII b)

with the definitions as for formula (VII).

Corresponding pretreatment agents used according to the present invention are those which contain at least one 4-morpholinomethyl-substituted silicone that comprises structural units of formula (VIII)

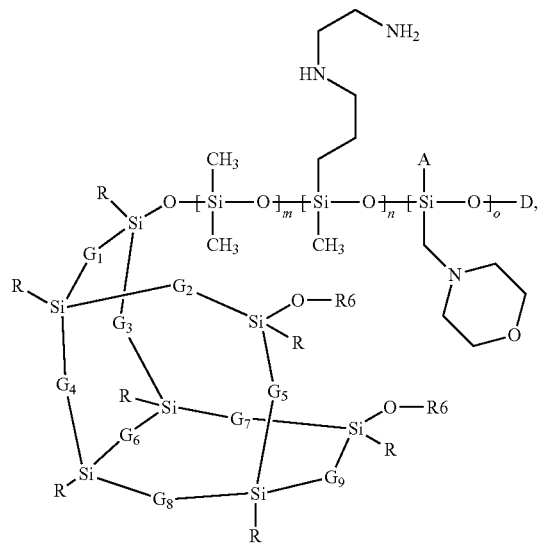
(VIII)

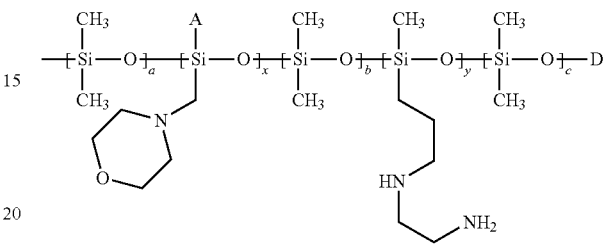

where the siloxane units m, n, and o resp. a, b, c, x, and y are present in statistically distributed fashion.

Particularly preferred pretreatment agents used according to the present invention contain at least one silicone of the following formula (VIII a)

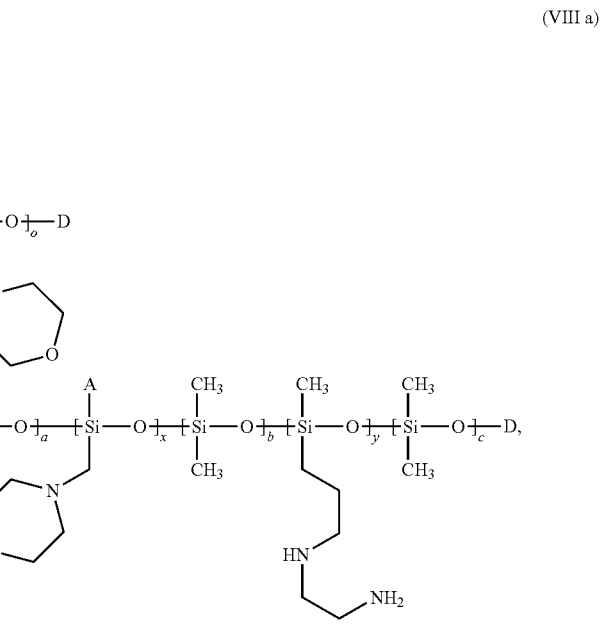
(VIII a)

half of an oxygen atom connecting to a structural unit (III), or denotes —OH,

D denotes an —H, —Si(CH$_3$)$_3$, —Si(CH$_3$)$_2$OH, —Si(CH$_3$)$_2$OCH$_3$ group, G1 to G9 mutually independently denote —O— or an —[—Si(CH$_3$)$_2$—O]$_m$ group where m=1 to 200, R denotes a 4-morpholinomethyl residue, R6 denotes —H or the grouping in which A denotes a structural unit (I), (II), or (III) bound via —O—, or an oligomeric or polymeric residue bound via —O— containing structural units of formulas (I), (II), or (III), or with the definitions as for formula (VIII).

Very particularly preferred pretreatment agents used according to the present invention contain at least one silicone of the following formula (VIII b)

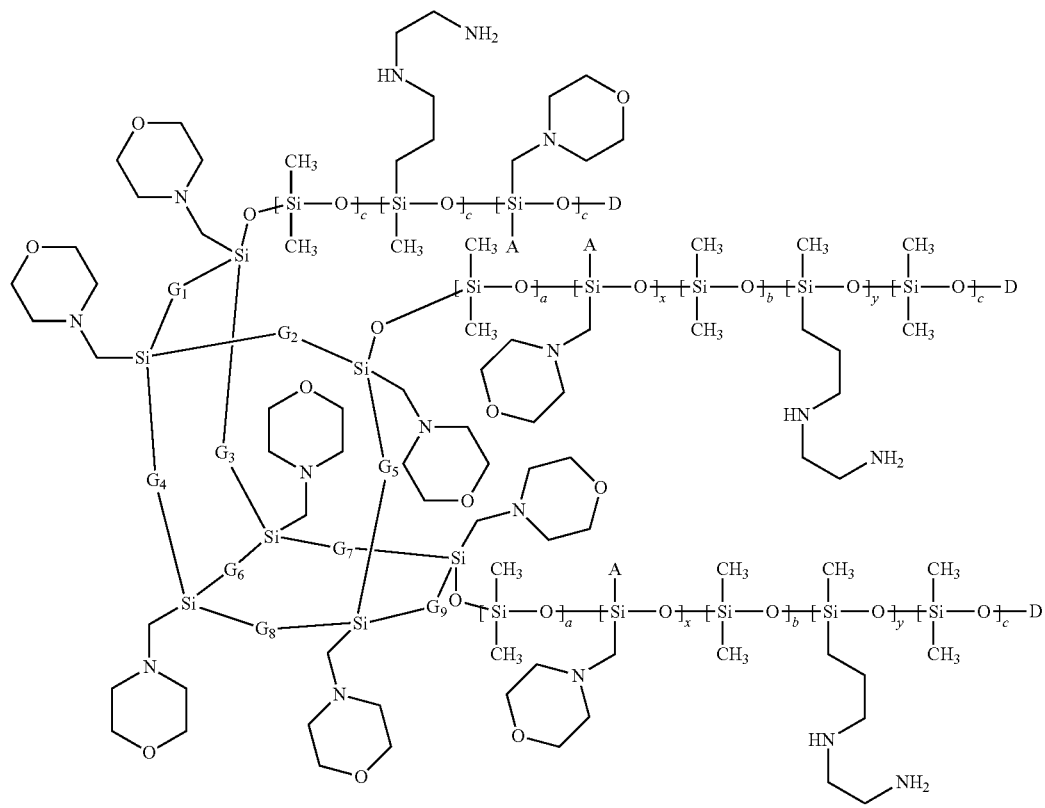

(VIIIb)

with the definitions as for formula (VIII).

Regardless of which special 4-morpholinomethyl-substituted silicone is contained in the pretreatment agents used according to the present invention, pretreatment agents that contain a 4-morpholinomethyl-substituted silicone in which more than about 50 mol % of the structural units are dimethylsiloxy units, i.e. in which structural unit (I) makes up at least half of all structural units of the silicone used, are preferred for the method according to the present invention.

In other words, silicones in which m>(n+o) resp. (a+b+c)>(n+o), are preferred.

Even further preferred pretreatment agents used according to the present invention contain a 4-morpholinomethyl-substituted silicone in which more than about 87.5 mol % of the structural units are dimethylsiloxy units, i.e. in which structural unit (I) makes up more than about 875 thousandths of all structural units of the silicone used.

In other words, silicones in which m>8(n+o) resp. (a+b+c)>8(n+o), are preferred.

Even further preferred pretreatment agents used according to the present invention contain a 4-morpholinomethyl-substituted silicone in which more than about 96 mol % of the structural units are dimethylsiloxy units, i.e. in which structural unit (I) makes up at least ninety-six hundredths of all structural units of the silicone used.

In other words, silicones in which m>25(n+o) resp. (a+b+c)>25(n+o), are preferred.

Even further preferred pretreatment agents used according to the present invention contain a 4-morpholinomethyl-substituted silicone in which more than about 98.7 mol % of the structural units are dimethylsiloxy units, i.e. in which structural unit (I) makes up at least nine hundred eighty-seven thousandths of all structural units of the silicone used.

In other words, silicones in which m>77(n+o) resp. (a+b+c)>77(n+o), are preferred.

Even further preferred pretreatment agents used according to the present invention contain a 4-morpholinomethyl-substituted silicone in which more than about 99.5 mol % of the structural units are dimethylsiloxy units, i.e. in which structural unit (I) makes up at least nine hundred ninety-five thousandths of all structural units of the silicone used.

In other words, silicones in which m>200(n+o) resp. (a+b+c)>200(n+o), are preferred.

In summary, preferred pretreatment agents used according to the present invention are characterized in that they contain at least one 4-morpholinomethyl-substituted silicone in which m>(n+o) resp. (a+b+c)>(n+o), preferably
m>8(n+o) resp. (a+b+c)>8(n+o), particularly preferably
m>25(n+o) resp. (a+b+c)>25(n+o), more preferably
m>77(n+o) resp. (a+b+c)>77(n+o), and in particular
m>200(n+o) resp. (a+b+c)>200(n+o).

A further method preferred according to the present invention is characterized in that the pretreatment agent used in step a) contains hydroxy-terminated 4-morpholinomethyl-substituted silicone(s) in which the molar ratio of hydroxy to alkoxy is in the range from about 0.2:1 to about 0.4:1, preferably in the range from about 1:0.8 to about 1:1.1.

A further method preferred according to the present invention is characterized in that the weight-average molar mass of the 4-morpholinomethyl-substituted silicone of formula (V) used in step a) is in the range from about 2000 to about 1,000,000 grams per mol (gmol$^{-1}$), preferably in the range from about 5000 to about 200,000 gmol$^{-1}$.

The average molar masses of amino-substituted silicones are measurable, for example, by gel permeation chromatography (GPC) at room temperature in polystyrene. Styragel μ columns can be selected as columns, THF as an eluent, and about 1 ml/min as a flow rate. Detection is accomplished preferably by refractometry using a UV meter.

4-Morpholinomethyl-substituted silicones of formula (V) that are particularly preferred according to the present invention are contained in the raw material Belsil ADM 8301 E (ex Wacker Silicones) under the name Amodimethicone/Morpholinomethyl Silsesquioxane. Belsil ADM 8301 E represents a microemulsion and is made up of the following constituents: Amodimethicone/Morpholinomethyl Silsesquioxane (about 10 wt %); Trideceth-5 (about 5 wt %); glycerol (about 2.5 wt %); phenoxyethanol (about 0.45 wt %); and water (about 82.05 wt %).

It has become apparent that the method according to the present invention can be further improved if specific nonionic components are likewise contained in the pretreatment agents used according to the present invention. These nonionic components moreover have positive effects on the shelf stability of the pretreatment agents used according to the present invention. Nonionic components that are particularly suitable here are ethoxylates of decanol, undecanol, dodecanol, tridecanol, myristyl alcohol, cetyl alcohol, and/or stearyl alcohol. Ethoxylated tridecanols have proven to be particularly suitable, and are incorporated with particular preference into the pretreatment agents used according to the present invention. Branched ethoxylated tridecanols are particularly preferred, in particular branched tridecanols having 3 to 5 ethylene oxide units in the molecule. Pretreatment agents used particularly preferably according to the present invention contain, based in each case on their weight, about 0.001 to about 5 wt %, preferably about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol, particularly preferably about 0.001 to about 5 wt %, preferably about 0.005 to about 3.5 wt %, particularly preferably about 0.01 to about 2 wt %, more preferably about 0.05 to about 1 wt %, and in particular about 0.1 to about 0.5 wt % branched ethoxylated tridecanol having 3 to 5 ethylene oxide units in the molecule.

Further surfactants and emulsifier agents are preferably not contained, or are contained only in small quantities, in the pretreatment agents used according to the present invention. Pretreatment agents used preferably according to the present invention contain, based on the total weight of the agent, about 0.001 to a maximum of about 6 wt % surfactant(s), the aforementioned ethoxylates of decanol, undecanol, dodecanol, tridecanol, myristyl alcohol, cetyl alcohol, and/or stearyl alcohol being included.

The pretreatment agents used according to the present invention are preferably of low viscosity, i.e. are formulated with a viscosity (measured at 20° C.) in the range from about 10 to about 2000 mPas, preferably about 20 to about 1000 mPas, particularly preferably about 50 to about 800 mPas. It has moreover been found that thickening polymers can attenuate the effect according to the present invention, so that preferred pretreatment agents used according to the present invention are characterized in that they contain thickening polymers in a total quantity of ≤about 2.5 wt %, preferably ≤about 1 wt %, more preferably ≤about 0.5 wt %, and in particular ≤about 0.01 wt %, based in each case on the weight of the pretreatment agent.

The pretreatment agents used according to the present invention can contain further ingredients. It is preferred in this context to use polyvalent alcohols that have moisture-donating properties. Pretreatment agents used according to the present invention that contain at least one polyvalent alcohol, preferably selected from the group of sorbitol and/or glycerol and/or 1,2-propylene glycol or mixtures thereof, in a total quantity from about 0.05 to about 15 wt %, preferably about 0.1 to about 10 wt %, particularly preferably about 0.15 to about 5 wt %, and in particular about 0.15 to about 1 wt %, based in each case on the weight of the pretreatment agent, are preferred here. For specific utilization sectors it can be advantageous to use only one of the three aforementioned preferred polyvalent alcohols. In most cases, glycerol is preferred. Mixtures of two of the three polyvalent alcohols, or of all three polyvalent alcohols, can nevertheless be preferred in other utilization sectors. A mixture of glycerol, sorbitol, and 1,2-propylene glycol at a weight ratio of about 1:(0.5-1):(0.1-0.5) has proven particularly advantageous here.

Besides sorbitol, glycerol, and 1,2-propylene glycol, further polyvalent alcohols that are suitable are those having at least 2OH groups, preferably mannitol, xylitol, polyethylene glycol, polypropylene glycol, and mixtures thereof. Among these compounds those having 2 to 12OH groups, and in particular those having 2, 3, 4, 5, 6, or 10OH groups, are preferred.

Polyhydroxy compounds having 2OH groups are, for example, glycol ($CH_2(OH)CH_2OH$) and other 1,2-diols such as $H—(CH_2)_n—CH(OH)CH_2OH$ where n=2, 3, 4, 5, 6, 7, 8, 9, 10, 11, 12, 13, 14, 15, 16, 17, 18, 19, 20. 1,3-Diols such as $H—(CH_2)_n—CH(OH)CH_2CH_2OH$, where n=1, 2, 3, 4, 5, 6, 7, 8, 9, 10, 11, 12, 13, 14, 15, 16, 17, 18, 19, 20, are also usable according to the present invention. The (n,n+1)-resp. (n,n+2)-diols having non-terminal OH groups can likewise be used. Important representatives of polyhydroxy compounds having 2OH groups are also the polyethylene and polypropylene glycols. Further preferred polyvalent alcohols that can be used are, for example, xylitol, propylene glycols, polyethylene glycols, in particular those having average molecular weights from 200 to 800. It is particularly preferred to use glycerol, so that agents that contain no other polyvalent alcohols besides glycerol are particularly preferred.

The use of specific care-providing substances in the pretreatment agents of the method according to the present invention is preferred in terms of pretreatment prior to an oxidative coloring treatment.

Pretreatment agents preferably used according to the present invention are characterized in that they additionally contain care-providing substance(s) in a total quantity from about 0.001 to about 10 wt %, preferably about 0.005 to about 7.5 wt %, particularly preferably about 0.01 to about 5 wt %, and in particular about 0.05 to about 2.5 wt %, based in each case on the total weight of the pretreatment agent. Preferred care-providing substance(s) are selected from at least one of the groups recited below:
   i. L-carnitine and/or salts thereof;
   ii. taurine and/or salts thereof;
   iii. niacinamide;
   iv. ubiquinone;
   v. ectoin;
   vi. vitamins;
   vii. flavonoids.

Pretreatment agents used according to the present invention can particularly preferably contain one or more amino acids as a further ingredient. Amino acids usable particularly preferably according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-Cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide L-trans-4-hydroxyproline, L-5-oxoproline (L-pyroglutamic acid), L-phosphoserine, creatine, 3-methyl-L-histidine, L-ornithine; both the individual amino acids and mixtures can be used.

Preferred pretreatment agents used according to the present invention contain one or more amino acids in narrower quantity ranges. Pretreatment agents used according to the present invention are characterized here in that they contain as a care-providing substance about 0.01 to about 5 wt %, preferably about 0.02 to about 2.5 wt %, particularly preferably about 0.05 to about 1.5 wt %, more preferably about 0.075 to about 1 wt %, and in particular about 0.1 to about 0.25 wt % amino acid(s), preferably from the group of glycine and/or alanine and/or valine and/or lysine and/or leucine and/or threonine, based in each case on the total weight of the pretreatment agent.

The pretreatment agent used according to the present invention can be formulated as a low-viscosity water-based emulsion, a spray, a cream, gel, lotion, paste, shampoo, or conditioner.

The method according to the present invention encompasses the application of a pretreatment agent onto keratinic fibers, and an oxidative coloring treatment subsequent thereto within a time period from about one second to about 24 hours.

A great advantage of the pretreatment agents used in step a) is that they are not only effective when utilized immediately prior to the oxidative coloring treatment, but instead can be utilized up to about 24 hours previously with no risk of attenuation of the effect due to external influences. It is thereby possible, for example, to carry out step a) of the method according to the present invention in the morning after shampooing, and to perform the oxidative coloring treatment only in the evening.

Methods preferred according to the present invention are characterized in that the time period between method steps a) and b) is from about 2 seconds to about 20 minutes, preferably about 30 seconds to about 10 minutes, particularly preferably about 1 to about 5 minutes.

Further methods preferred according to the present invention are characterized in that the pretreatment agent applied in method step a) is allowed to act on the hair for a time period from about 2 seconds to about 120 minutes, preferably about 5 seconds to about 10 minutes, before method step b) occurs.

Further methods preferred according to the present invention are characterized in that the pretreatment agent applied in method step a) is allowed to act on the hair for a time period from about 2 seconds to about 120 minutes, preferably about 5 seconds to about 10 minutes, before at least one of the following method steps a)i, which occur before method step b), occurs:
  rinsing out the hair;
  drying the hair with a towel;
  allowing the hair to air-dry;
  blow-drying the hair;
  drying the hair with a drying hood;
  combinations of the aforementioned method steps.

The drying operation occurs preferably at a temperature from about 20° C. to about 150° C.

Particularly preferably, the drying operation resp. operations are not preceded by rinsing out of the hair. A method preferred according to the present invention is therefore characterized in that no rinsing out of the hair occurs between the application of the pretreatment agent performed in method step a) and the drying operation resp. operations. It can, however, also be preferred according to the present invention first to rinse out the hair after step a) and then to dry it before the coloring step b) occurs.

The method preferred according to the present invention is further characterized in that step b) encompasses the application of a hair coloring agent that is obtained by mixing a composition (A), which contains at least one oxidation dye precursor of the developer type and at least one oxidation dye precursor of the coupler type, with a composition (B) that contains at least one oxidizing agent, where composition (B) additionally contains at least one cosmetic oil in a total quantity from about 10 to about 80 wt %, based on the weight of composition (B).

Composition (B) used in the method according to the present invention contains as a first obligatory ingredient at least one oxidizing agent. Preferred oxidizing agents are selected from peroxo compounds, preferably selected from hydrogen peroxide, a solid addition compound of hydrogen peroxide with inorganic or organic compounds, such as sodium perborate, sodium percarbonate, magnesium percarbonate, sodium percarbamide, polyvinylpyrrolidone.$nH_2O_2$ (n is a positive number greater than 0), urea peroxide, and melamine peroxide, furthermore selected from diammonium peroxodisulfate (also referred to as ammonium persulfate), disodium peroxodisulfate (also referred to as sodium persulfate), and dipotassium peroxodisulfate (also referred to as potassium persulfate), and from mixtures of these oxidizing agents. Oxidizing agents used with very particular preference according to the present invention are aqueous hydrogen peroxide solutions. The concentration of a hydrogen peroxide solution is determined on the one hand by regulatory provisions and on the other hand by the desired effect; about 6- to about 12-weight-percent solutions in water are preferably used. Methods preferred according to the present invention are characterized in that the composition (B) that is used contains, based on its weight, about 1 to about 24 wt %, preferably about 4 to about 10 wt %, particularly preferably about 3 to about 6 wt % hydrogen peroxide (calculated as 100% $H_2O_2$).

For oxidative hair coloring methods, it is usual that shortly before application into the hair, a coloring composition that contains one or more oxidation dye precursors and optionally one or more substantive dyes is mixed with an aqueous oxidizing-agent-containing composition to yield a ready-to-use hair coloring agent, and is then applied onto the hair. The coloring composition and the oxidizing-agent-containing composition are usually coordinated with one another in such a way that with a mixing ratio of about 1 to 1 (based on parts by weight) an initial concentration of hydrogen peroxide from about 0.5 to about 12 wt %, preferably about 2 to about 10 wt %, particularly preferably about 3 to about 6 wt % hydrogen peroxide (calculated as 100% $H_2O_2$) is present in the hair coloring agent, based on the weight of the hair coloring agent. It is, however, equally possible to coordinate the coloring composition and the oxidizing-agent-containing composition with one another in such a way that the concentrations necessary in the ready-to-use coloring agent are obtained by means of mixing ratios other than 1:1, for example by a weight-related mixing ratio of 1:2 or 1:3 or even 2:3. Methods preferred according to the present invention are characterized in that the ready-to-use hair coloring agent used in method step b) contains an initial quantity of hydrogen peroxide from about 0.5 to about 12 wt %, preferably about 2 to about 10 wt %, particularly preferably about 3 to about 6 wt % hydrogen peroxide (calculated as 100% $H_2O_2$), based on the weight of the hair coloring agent.

Further methods preferred according to the present invention are characterized in that the ready-to-use hair coloring agent used in method step b) contains at least one cosmetic oil in a total quantity from about 5 to about 50 wt %, preferably about 8 to about 40 wt %, particularly preferably about 12 to about 30 wt %, extraordinarily preferably about 15 to about 25 wt %, based in each case on the weight of the hair coloring agent.

Oxidative coloring processes on keratin fibers usually proceed in an alkaline environment. In order to minimize stress on the keratin fibers and also on the skin, however, it is not desirable to establish too high a pH. It is therefore preferred if the pH of the ready-to-use hair coloring agent used in step b) is between about 7 and about 11, in particular in the range from about 8 to about 10.5. The pH values for purposes of the present invention are pH values that have been measured at a temperature of about 22° C.

The alkalizing agents usable according to the present invention in order to establish the preferred pH can be selected from the group of ammonia, basic amino acids, alkali hydroxides, alkanolamines, alkali metal metasilicates, alkali phosphates, and alkali hydrogen phosphates. Lithium, sodium, potassium preferably serve as alkali metal ions, in particular sodium or potassium.

The basic amino acids usable as alkalizing agents are preferably selected from the group of L-arginine, D-arginine, D,L-arginine, L-lysine, D-lysine, D,L-lysine, particularly preferably L-arginine, D-arginine, D,L-arginine used as an alkalizing agent for purposes of the invention.

The alkali hydroxides usable as alkalizing agents are preferably selected from the group of sodium hydroxide and potassium hydroxide.

The alkanolamines usable as alkalizing agents are preferably selected from primary amines having a $C_2$ to $C_6$ alkyl basic structure that carries at least one hydroxyl group. Particularly preferred alkanolamines are selected from the group that is constituted from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines very particularly preferred according to the present invention are selected from the group of: 2-aminoethan-1-ol, 2-amino-2-methylpropan-1-ol, and 2-amino-2-methylpropane-1,3-diol.

The use of hydrogen peroxide or addition products thereof with organic resp. inorganic compounds is often insufficient for a coloring operation that requires considerable lightening of very dark hair. A combination of hydrogen peroxide and peroxodisulfate salts (persulfate salts) is generally used in such cases. Preferred persulfate salts are ammonium peroxydisulfate, potassium peroxydisulfate, sodium peroxydisulfate, and mixtures thereof.

The at least one persulfate salt is contained preferably in a total quantity from about 0.1 to about 25 wt %, particularly preferably in a total quantity from about 1 to about 15 wt %, based on the weight of the ready-to-use coloring agent.

As a further obligatory component, the composition (B) used according to the present invention contains at least one cosmetic oil in a total quantity from about 10 to about 80 wt %, based on the weight of composition (B). The cosmetic oil is liquid under standard conditions (20° C., 1013.25 mbar); essential oils and perfume oils resp. fragrances are not included among the cosmetic oils. The cosmetic oils that are liquid under standard conditions are not miscible with water. "Essential oils" are understood according to the present invention as mixtures of volatile components that are produced by steam distillation from vegetable raw materials, e.g. citrus oils. When a "cosmetic oil" is discussed in the present Application, this always refers to a cosmetic oil that is not a fragrance and not an essential oil, is liquid under standard conditions, and is not miscible with water.

The definition of a "fragrance" for purposes of the present Application corresponds to the definition usual in the art, as may be gathered from the RÖMPP Chemie Lexikon [Chemical Lexicon] as of December 2007. According to the latter, a fragrance is a chemical compound having an odor and/or taste that excites the receptors of the hair cells of the olfactory system (adequate stimulus). The physical and chemical properties necessary for this are a low molar mass of at most about 300 g/mol, a high vapor pressure, minimal water solubility and high lipid solubility, as well as weak polarity and the presence of at least one osmophoric group in the molecule. In order to distinguish volatile low-molecular-weight substances that are usually (and also for purposes of the present Application) viewed and utilized not as fragrances but instead principally as solvents, for example ethanol, propanol, isopropanol, and acetone, from fragrances according to the present invention, fragrances according to the present invention have a molar mass from about 74 to about 300 g/mol, contain at least one osmophoric group in the molecule, and have an odor and/or taste, i.e. they excite the receptors of the hair cells of the olfactory system.

Cosmetic oils preferred according to the present invention are selected from natural and synthetic hydrocarbons, particularly preferably from paraffin oils, $C_{18}$ to $C_{30}$ isoparaffins, in particular isoeicosane, polyisobutenes, and polydecenes, which are obtainable, for example, under the name Emery® 3004, 3006, 3010 or under the name Ethylflo® from Albemarle or Nexbase® 2004G from Nestle, further selected from $C_8$ to $C_{16}$ isoparaffins, in particular from isodecane, isododecane, isotetradecane, and isohexadecane as well as mixtures thereof, as well as 1,3-di-(2-ethylhexyl)cyclohexane (obtainable e.g. under the trade name Cetiol® S from BASF).

Further cosmetic oils preferred according to the present invention are selected from benzoic acid esters of linear or branched $C_{8-22}$ alkanols. Benzoic acid $C_{12}$ to $C_{15}$ alkyl esters, obtainable e.g. as the commercial product Finsolv® TN, benzoic acid isostearyl esters, obtainable e.g. as the commercial product Finsolv® SB, ethylhexyl benzoate, obtainable e.g. as the commercial product Finsolv® EB, and benzoic acid octyldodecyl esters, obtainable e.g. as the commercial product Finsolv® BOD, are particularly preferred.

Further cosmetic oils preferred according to the present invention are selected from fatty alcohols having 6 to 30 carbon atoms, which are unsaturated or branched and saturated or branched and unsaturated. The branched alcohols are often also referred to as "Guerbet alcohols," since they are obtainable via the Guerbet reaction. Preferred alcohol oils are 2-hexyldecanol (Eutanol® G 16), 2-octyldodecanol (Eutanol® G), 2-ethyhexyl alcohol, and isostearyl alcohol.

Further preferred cosmetic oils are selected from mixtures of Guerbet alcohols and Guerbet alcohol esters, e.g. the commercial product Cetiol® PGL (2-hexyldecanol and 2-hexyldecyl laurate).

Further cosmetic oils preferred according to the present invention are selected from triglycerides (=triesters of glycerol) of linear or branched, saturated or unsaturated, optionally hydroxylated $C_{8-30}$ fatty acids. The use of natural oils, e.g. amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, linseed oil, macadamia nut oil, corn oil, almond oil, marula oil, evening primrose oil, olive oil, palm oil, palm kernel oil, para nut oil, pecan nut oil, peach kernel oil, rapeseed oil, castor oil, sea buckthorn pulp oil, sea buckthorn seed oil, sesame oil, soy oil, sunflower oil, grapeseed oil, walnut oil, wild rose oil, wheat germ oil, and the liquid components of coconut oil and the like, can be particularly preferred. Synthetic triglyceride oils are also preferred, however, in particular Capric/Caprylic Triglycerides, e.g. the commercial products Myritol® 318, Myritol® 331 (BASF), or Miglyol® 812 (Hills) having unbranched fatty acid esters, as well as glyceryl triisostearine having branched fatty acid esters.

Further cosmetic oils particularly preferred according to the present invention are selected from dicarboxylic acid esters of linear or branched $C_2$ to $C_{10}$ alkanols, in particular diisopropyl adipate, di-n-butyl adipate, di-(2-ethylhexyl)adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl)succinate.

Further cosmetic oils particularly preferred according to the present invention are selected from esters of linear or branched, saturated or unsaturated fatty alcohols having 2 to 30 carbon atoms with linear or branched, saturated or unsaturated fatty acids having 2 to 30 carbon atoms, which can be hydroxylated. These include 2-hexyldecyl stearate (Eutanol® G 16 S), 2-hexyldecyl laurate, isodecyl neopentanoate, isononyl isononanoate, 2-ethylhexyl palmitate (Cegesoft® C 24), and 2-ethylhexyl stearate (Cetiol® 868). Also preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further cosmetic oils preferred according to the present invention are selected from addition products of 1 to 5 propylene oxide units with mono- or polyvalent $C_{8-22}$ alkanols such as octanol, decanol, decanediol, lauryl alcohol, myristyl alcohol, and stearyl alcohol, e.g. PPG-2 Myristyl Ether and PPG-3 Myristyl Ether (Witconol® APM).

Further cosmetic oils preferred according to the present invention are selected from addition products of at least 6 ethylene oxide and/or propylene oxide units with mono- or polyvalent $C_{3-22}$ alkanols such as glycerol, butanol, butanediol, myristyl alcohol, and stearyl alcohol, which can be esterified if desired, e.g. PPG-14 Butyl Ether (Ucon Fluid® AP), PPG-9 Butyl Ether (Breox® B25), PPG-10 Butanediol (Macol® 57), PPG-15 Stearyl Ether (Arlamol® E), and glycereth-7 diisonoanoate.

Further cosmetic oils preferred according to the present invention are selected from $C_8$ to $C_{22}$ fatty alcohol esters of monovalent or polyvalent $C_2$ to $C_7$ hydroxycarboxylic acids, in particular the esters of glycolic acid, lactic acid, malic acid, tartaric acid, citric acid, and salicylic acid. Such esters based on linear $C_{14/15}$ alkanols, e.g. $C_{12}$ to $C_{15}$ alkyl lactate, and on $C_{12/13}$ alkanols branched in the 2-position, can be obtained under the trade name Cosmacol® from Nordmann, Rassmann GmbH & Co., Hamburg, in particular the commercial products Cosmacol® ESI, Cosmacol® EMI, and Cosmacol® ETI.

Further cosmetic oils preferred according to the present invention are selected from symmetrical, asymmetrical, or cyclic esters of carbonic acid with $C_{3-22}$ alkanols, $C_{3-22}$ alkanediols, or $C_{3-22}$ alkanetriols, e.g. dicaprylyl carbonate (Cetiol® CC), or the esters according to the teaching of DE 19756454 A1, in particular glycerol carbonate.

Further cosmetic oils that can be preferred according to the present invention are selected from esters of dimers of unsaturated $C_{12}$ to $C_{22}$ fatty acids (dimer fatty acids) with monovalent linear, branched, or cyclic $C_2$ to $C_{18}$ alkanols or with polyvalent linear or branched $C_2$ to $C_6$ alkanols.

Further cosmetic oils that are suitable according to the present invention are selected from among the silicone oils that include, for example, dialkyl- and alkylarylsiloxanes such as e.g. cyclopentasiloxane, cyclohexasiloxane, dimethylpolysiloxane, and methyphenylpolysiloxane, but also hexamethyldisiloxane, octamethyltrisiloxane, and decamethyltetrasiloxane. Volatile silicone oils, which can be cyclic, can be preferred, for example octamethylcyclotetrasiloxane, decamethylcyclopentasiloxane, and dodecamethylcyclohexasiloxane, as well as mixtures thereof such as those contained, for example, in the commercial products DC 244, 245, 344, and 345 of Dow Corning. Also suitable are volatile linear silicone oils, in particular hexamethyldisiloxane ($L_2$), octamethyltrisiloxane ($L_3$), decamethyltetrasiloxane ($L_4$), as well as any mixtures of two or three of $L_2$, $L_3$, and/or $L_4$, preferably mixtures such as those contained e.g. in the commercial products DC2-1184, Dow Corning® 200 (0.65 cSt), and Dow Corning® 200 (1.5 cSt) of Dow Corning. Preferred nonvolatile silicone oils are selected, from higher-molecular-weight linear dimethylpolysiloxanes, obtainable commercially e.g. under the name Dow Corning® 190, Dow Corning® 200 Fluid, having kinematic viscosities (25° C.) in the range from about 5 to about 100 cSt, preferably about 5 to about 50 cSt, or even about 5 to about 10 cSt, and dimethylpolysiloxane having a kinematic viscosity (25° C.) of approximately 350 cSt.

It can be extraordinarily preferred according to the present invention to use mixtures of the aforementioned cosmetic oils.

Preferred compositions (B) used according to the present invention are characterized in that the cosmetic oil is selected from natural and synthetic hydrocarbons, particularly preferably from paraffin oils, $C_{18}$ to $C_{30}$ isoparaffins, in particular isoeicosane, polyisobutenes, and polydecenes, $C_8$ to $C_{16}$ isoparaffins, and 1,3-di-(2-ethylhexyl)cyclohexane; benzoic acid esters of linear or branched $C_{8-22}$ alkanols; fatty alcohols having 6 to 30 carbon atoms, which are unsaturated or branched and saturated or branched and unsaturated; triglycerides of linear or branched, saturated or unsaturated, optionally hydroxylated $C_{8-30}$ fatty acids, in particular natural oils; dicarboxylic acid esters of linear or branched $C_2$ to $C_{10}$ alkanols; esters of linear or branched, saturated or unsaturated fatty alcohols having 2 to 30 carbon atoms with linear or branched, saturated or unsaturated fatty acids having 2 to 30 carbon atoms, which can be hydroxylated; addition products of 1 to 5 propylene oxide units with mono- or polyvalent $C_{8-22}$ alkanols; addition products of at least 6 ethylene oxide and/or propylene oxide units with mono- or polyvalent $C_{3-22}$ alkanols; $C_8$ to $C_{22}$ fatty alcohol esters of monovalent or polyvalent $C_2$ to $C_7$ hydroxycarboxylic acids; symmetrical, asymmetrical, or cyclic esters of carbonic acid with $C_{3-22}$ alkanols, $C_{3-22}$ alkanediols, or $C_{3-22}$ alkanetriols; esters of dimers of unsaturated $C_{12}$ to $C_{22}$ fatty acids (dimer fatty acids) with monovalent linear, branched, or cyclic $C_2$ to $C_{18}$ alkanols or with polyvalent linear or branched $C_2$ to $C_6$ alkanols; silicone oils; and mixtures of the aforementioned substances.

Preferred methods according to the present invention are characterized in that the composition (B) used according to the present invention contains at least one cosmetic oil in a total quantity from about 12 to about 70 wt %, preferably about 14 to about 60 wt %, particularly preferably about 15 to about 52 wt %, and extraordinarily preferably about 17 to about 35 wt %, based in each case on the weight of composition (B).

Further preferred methods according to the present invention are characterized in that the composition (B) used according to the present invention contains at least one surfactant.

When selecting surfactants suitable according to the present invention, it is particularly preferred to use a mixture of surfactants in order to allow optimum adjustment of the stability of the oxidizing agent compositions (B) used according to the present invention.

Preferred methods according to the present invention are characterized in that the surfactant contained in composition (B) is selected from nonionic surfactants and anionic surfactants and from mixtures thereof. Nonionic surfactants used with particular preference are selected from castor oil ethoxylated with about 20 to about 100 mol ethylene oxide per mol, ethoxylated $C_8$ to $C_{24}$ alkanols having about 10 to about 100 mol ethylene oxide per mol, ethoxylated $C_8$ to $C_{24}$ carboxylic acids having about 10 to about 100 mol ethylene oxide per mol, sorbitan monoesters, ethoxylated with about 20 to about 100 mol ethylene oxide per mol, of linear saturated and unsaturated $C_{12}$ to $C_{30}$ carboxylic acids, which can be hydroxylated, in particular those of myristic acid, palmitic acid, stearic acid, or mixtures of these fatty acids, alkylmono- and -oligoglycosides having 8 to 22 carbon atoms in the alkyl residue and ethoxylated analogs thereof, and mixtures of the aforesaid substances.

Castor oil ethoxylated with about 40 to about 80 mol ethylene oxide per mol is preferably contained in the compositions (B) preferably used according to the present invention.

The ethoxylated $C_8$ to $C_{24}$ alkanols have the formula $R^1O(CH_2CH_2O)_nH$, where $R^1$ denotes a linear or branched alkyl residue and/or alkenyl residue having 8 to 24 carbon atoms, and n (the average number of ethylene oxide units per molecule) denotes numbers from about 10 to about 100, preferably about 10 to about 30, particularly preferably about 15 to about 25 mol ethylene oxide per 1 mol caprylyl alcohol, 2-ethylhexyl alcohol, capryl alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and brassidyl alcohol, as well as industrial mixtures thereof. Adducts of about 10 to about 100 mol ethylene oxide with industrial fatty alcohols having 12 to 18 carbon atoms, for example coconut, palm, palm kernel, or tallow fatty alcohol, are also suitable. Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20, and Coceth-30, are particularly preferred.

The ethoxylated $C_8$ to $C_{24}$ carboxylic acids have the formula $R^1O(CH_2CH_2)_nH$, where $R^1O$ denotes a linear or branched, saturated or unsaturated acyl residue having 8 to 24 carbon atoms, and n (the average number of ethylene oxide units per molecule) denotes numbers from about 10 to about 100, preferably about 10 to about 30 mol ethylene oxide per 1 mol caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachidic acid, gadoleic acid, behenic acid, erucic acid, and brassidic acid, as well as industrial mixtures thereof. Adducts of 10 to 100 mol ethylene oxide with industrial fatty acids having 12 to 18 carbon atoms, for example coconut, palm, palm kernel, or tallow fatty acid, are also suitable. PEG-50 monostearate, PEG-100 monostearate, PEG-50 monooleate, PEG-100 monooleate, PEG-50 monolaurate, and PEG-100 monolaurate are particularly preferred.

Preferred sorbitan monoesters, ethoxylated with about 20 to about 100 mol ethylene oxide per mol, of linear saturated and unsaturated $C_{12}$ to $C_{30}$ carboxylic acids, which can be hydroxylated, are selected from Polysorbate-20, Polysorbate-40, Polysorbate-60, and Polysorbate-80.

$C_8$ to $C_{22}$ alkylmono- and -oligoglycosides are also preferably used. $C_8$ to $C_{22}$ alkylmono- and -oligoglycosides represent known, commercially usual surfactants and emulsifier agents. They are manufactured in particular by reacting glucose or oligosaccharides with primary alcohols having 8 to 22 carbon atoms. With regard to the glycoside residue, both monoglycosides in which a cyclic sugar residue is bound glycosidically to the fatty alcohol, and oligomeric glycosides having a degree of oligomerization up to approximately 8, preferably about 1 to about 2, are suitable. The degree of oligomerization is a statistical average that is based on a homolog distribution that is usual for industrial products of this kind. Products that are obtainable under the name Plantacare® contain a glycosidically bound $C_8$ to $C_{16}$ alkyl group on an oligoglucoside residue whose average degree of oligomerization is about 1 to about 2, in particular about 1.2 to about 1.4. Particularly preferred $C_8$ to $C_{22}$ alkyl mono- and -oligoglycosides are selected from octyl glucoside, decyl glucoside, lauryl glucoside, palmityl glucoside, isostearyl glucoside, stearyl glucoside, arachidyl glucoside, and behenyl glucoside, as well as mixtures thereof. The acyl glucamides derived from glucamine are also suitable as nonionic oil-in-water emulsifier agents.

Anionic surfactants suitable in the compositions (B) used according to the present invention are all anionic surface-active substances suitable for use on the human body, which comprise an anionic group imparting water solubility, for example a carboxylate, sulfate, sulfonate, or phosphate group, and a lipophilic alkyl group having approximately 8 to 30 carbon atoms, preferably about 8 to about 24 carbon atoms, in the molecule. Glycol ether or polyglycol ether groups, ester, ether, and amide groups, and hydroxyl groups can additionally be contained in the molecule. Examples of suitable anionic surfactants are, in each case in the form of the sodium, potassium, and ammonium salts and the mono-, di, and trialkanolammonium salts having 2 to 4 carbon atoms in the alkanol group: linear and branched fatty acids having 8 to 30 carbon atoms (soaps), polyethoxylated ethercarboxylic acids, acyl sarcosides, acyl taurides, acyl isethionates, sulfosuccinic acid mono- and dialkyl esters and sulfosuccinic acid monoalkylpolyoxyethyl esters having 1 to 6 ethylene oxide groups, linear alkanesulfonates, linear alpha-olefinsulfonates, sulfonates of unsaturated fatty acids having up to 6 double bonds, alpha-sulfo fatty acid methyl esters of fatty acids, $C_8$ to $C_{20}$ alkyl sulfates and $C_8$ to $C_{20}$ alkyl ether sulfates having up to 15 oxyethyl groups, mixtures of surface-active hydroxysulfonates, sulfated hydroxyalkyl polyethylene glycol ethers and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, as well as monoglyceride sulfates and monoglyceride ether sulfates.

Preferred anionic surfactants are soaps, $C_8$ to $C_{20}$ alkyl sulfates, $C_8$ to $C_{20}$ alkyl ether sulfates, and $C_8$ to $C_{20}$ ether carboxylic acids having 8 to 20 carbon atoms in the alkyl group and up to 12 ethylene oxide groups in the molecule. Sodium cetearyl sulfate is particularly preferred.

Preferably the total quantity of at least one surfactant in the oxidizing agent composition (B) is about 0.1 to about 5 wt %, preferably about 0.5 to about 3 wt %, and particularly preferably about 1 to about 2 wt %, based in each case on the total weight of the oxidizing agent composition (B).

Particularly preferably, the oxidizing agent composition (B) used according to the present invention contains a total of about 0.1 to about 5 wt %, preferably about 0.5 to about 3 wt %, and particularly preferably about 1 to about 2 wt %, of a mixture of nonionic and anionic surfactants, based in each case on the total weight of the oxidizing agent composition (B).

Further preferred methods according to the present invention are characterized in that the composition (B) used according to the present invention contains at least one linear saturated alkanol having 12 to 30 carbon atoms.

Preferred linear saturated alkanols having 12 to 30 carbon atoms, in particular having about 16 to about 22 carbon atoms, are selected from cetyl alcohol, stearyl alcohol, arachidyl alcohol, behenyl alcohol, and lanolin alcohol, as well as mixtures of these alkanols. Alkanol mixtures particularly preferred according to the present invention are those obtainable upon industrial hydrogenation of vegetable and animal fatty acids. The total quantity in the oxidizing agent composition (B) of at least one linear saturated alkanol having 12 to 30 carbon atoms is about 0.1 to about 10 wt %, preferably about 0.5 to about 7 wt %, and particularly preferably about 3 to about 5 wt %, based in each case on the total weight of the oxidizing agent composition (B).

Further preferred methods according to the present invention are characterized in that the composition (B) used according to the present invention contains: about 1 to about 24 wt %, preferably about 4 to about 10 wt %, particularly preferably about 3 to about 6 wt % hydrogen peroxide (calculated as 100% $H_2O_2$), furthermore at least one cosmetic oil in a total quantity from about 12 to about 70 wt %, preferably about 14 to about 60 wt %, particularly preferably about 15 to about 52 wt %, and extraordinarily preferably about 17 to about 35 wt %, furthermore at least one surfactant in a total quantity from about 0.1 to about 5 wt %, preferably about 0.5 to about 3 wt %, and particularly preferably about 1 to about 2 wt %, as well as at least one linear saturated alkanol having 12 to 30 carbon atoms, in a total quantity from about 0.1 to about 10 wt %, preferably about 0.5 to about 7 wt %, and particularly preferably about 3 to about 5 wt %, where all "wt %" indications refer to the weight of composition (B).

The composition (A) used in the method according to the present invention contains as obligatory ingredients at least one oxidation dye precursor of the developer type and at least one oxidation dye precursor of the coupler type.

Oxidation dye precursors can be divided in terms of their reaction behavior into two categories: the so-called developer components and coupler components.

Coupler components alone do not produce any significant color in the context of oxidative coloring, but instead always require the presence of developer components. Developer components can form, with themselves, the actual dye.

The developer and coupler components are usually used in free form. In the case of substances having amino groups, however, it can be preferred to use them in salt form, in particular in the form of the hydrochlorides or hydrobromides or the sulfates.

It has been found, surprisingly, that hair coloring results with particularly good washing fastness could be achieved with the method according to the present invention using at least one oxidation dye precursor of the developer type and at least one oxidation dye precursor of the coupler type. A particularly good improvement in washing fastness was observed for formulations having the developer/coupler combination 1-hydroxyethyl-4,5-diaminopyrazole/3-aminophenol. The reduction in hair damage was also surprisingly large.

Particularly preferred developer components are selected from at least one compound of the group that is constituted from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N-bis-(2-hydroxyethyl)-N,N-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, the physiologically acceptable salts of these compounds, and mixtures of these developer components and developer component salts.

Very particularly preferred developer components are selected from 4,5-diamino-1-(2-hydroxyethyl)pyrazole, p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and mixtures of these compounds as well as physiologically acceptable salts thereof. 4,5-Diamino-1-(2-hydroxyethyl)pyrazole and physiologically acceptable salts thereof are extraordinarily preferred.

The developer components are used preferably in a total quantity from about 0.01 to about 20 wt %, particularly preferably about 0.2 to about 10 wt %, and extraordinarily preferably about 0.6 to about 5 wt %, based in each case on the weight of composition (A).

The developer components are used preferably in a total quantity from about 0.005 to about 10 wt %, particularly preferably about 0.1 to about 5 wt %, and extraordinarily preferably about 0.3 to about 2.5 wt %, based in each case on the weight of the ready-to-use coloring agent.

The term "ready-to-use coloring agent" is understood for purposes of this Application as the mixture of all oxidation dye precursors and all oxidizing agents, optionally in combination with a suitable cosmetic carrier, e.g. a cream base, and optionally in combination with at least one substantive dye.

Coupler components for purposes of the invention allow at least one chemical residue of the coupler to be substituted with the oxidized form of the developer component, in which context a covalent bond forms between the coupler component and developer component. Couplers are preferably cyclic compounds that carry on the cycle at least two groups selected from (i) optionally substituted amino groups, and/or (ii) hydroxyl groups. If the cyclic compound is a six-membered ring (preferably aromatic), the aforesaid groups are then located preferably in the ortho or meta position with respect to one another.

Preferred methods according to the present invention are characterized in that the at least one oxidation dye precursor of the coupler type is selected from one of the following classes:
- 3-aminophenol (m-aminophenol) and/or derivatives thereof,
- 3-aminoaniline (m-diaminobenzene) and/or derivatives thereof,
- 2-aminoaniline (1,2-diaminobenzene; o-diaminobenzene) and/or derivatives thereof,
- 2-aminophenol (o-aminophenol) and/or derivatives thereof,
- naphthalene derivatives having at least one hydroxy group,
- di-resp. trihydroxybenzene and/or derivatives thereof,
- pyridine derivatives,
- pyrimidine derivatives,
- monohydroxyindole derivatives and/or monoaminoindole derivatives,
- monohydroxyindoline derivatives and/or monoaminoindoline derivatives
- pyrazolone derivatives such as e.g. 1-phenyl-3-methylpyrazol-5-one,
- morpholine derivatives such as e.g. 6-hydroxybenzomorpholine or 6-aminobenzomorpholine,
- quinoxaline derivatives such as e.g. 6-methyl-1,2,3,4-tetrahydroquinoxaline.

Mixtures of two or more compounds from one or more of these classes are likewise preferred according to the present invention in the context of this embodiment.

Additional coupler components particularly preferred according to the present invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2'-hydroxyethylamino)benzene 2-amino-4-hydroxyethylaminoanisole), 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynapthalene, 4-hydroxyindole, 6-hydroxyindole, 7-hydroxyindole, 4-hydroxyindoline, 6-hydroxyindoline, 7-hydroxyindoline, or mixtures of these compounds, or the physiologically acceptable salts of the aforesaid compounds.

Very particularly preferred in this context are 3-aminophenol, resorcinol, 2-methylresorcinol, 5-amino-2-methylphenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, and 1-naphthol, as well as physiologically acceptable salts thereof and mixtures of the components recited.

The at least one coupler component is used preferably in a total quantity from about 0.01 to about 20 wt %, particularly preferably about 0.2 to about 10 wt %, and extraordinarily preferably about 0.6 to about 5 wt %, based in each case on the weight of composition (A).

The at least one coupler component is used preferably in a total quantity from about 0.005 to about 10 wt %, preferably about 0.1 to about 5 wt %, and extraordinarily preferably about 0.3 to about 2.5 wt %, based in each case on the weight of the ready-to-use oxidative coloring agent.

The following combinations of oxidation dye precursors of the developer type and of the coupler type are particularly preferred in the context of the present invention, where the amine compounds and the nitrogen heterocycles can also be present in the form of their physiologically acceptable salts:
- p-toluoylenediamine/resorcinol;
- p-toluoylenediamine/2-methylresoreinol;
- p-toluoylenediamine/5-amino-2-methylphenol;
- p-toluoylenediamine/3-aminophenol;
- p-toluoylenediamine/2-(2,4-diaminophenoxy)ethanol;
- p-toluoylenediamine/1,3-bis-(2,4-diaminophenoxy)propane;
- p-toluoylenediamine/1-methoxy-2-amino-4-(2-hydroxyethylamino)benzene;
- p-toluoylenediamine/2-amino-3-hydroxypyridine;
- p-toluoylenediamine/1-naphthol;
- 2-(2-hydroxyethyl)-p-phenylenediamine/resorcinol;
- 2-(2-hydroxyethyl)-p-phenylenediamine/2-methylresorcinol;
- 2-(2-hydroxyethyl)-p-phenylenediamine/5-amino-2-methylphenol;
- 2-(2-hydroxyethyl)-p-phenylenediamine/3-aminophenol;
- 2-(2-hydroxyethyl)-p-phenylenediamine/2-(2,4-diaminophenoxy)ethanol;
- 2-(2-hydroxyethyl)-p-phenylenediamine/1,3-bis-(2,4-diaminophenoxy)propane;
- 2-(2-hydroxyethyl)-p-phenylenediamine/1-methoxy-2-amino-4-(2-hydroxyethylamino)benzene;
- 2-(2-hydroxyethyl)-p-phenylenediamine/2-amino-3-hydroxypyridine;
- 2-(2-hydroxyethyl)-p-phenylenediamine/1-naphthol;
- 2-methoxymethyl-p-phenylenediamine/resorcinol;
- 2-methoxymethyl-p-phenylenediamine/2-methylresorcinol;
- 2-methoxymethyl-p-phenylenediamine/5-amino-2-methylphenol;
- 2-methoxymethyl-p-phenylenediamine/3-aminophenol;
- 2-methoxymethyl-p-phenylenediamine/2-(2,4-diaminophenoxy)ethanol;
- 2-methoxymethyl-p-phenylenediamine/1,3-bis-(2,4-diaminophenoxy)propane;
- 2-methoxymethyl-p-phenylenediamine/1-methoxy-2-amino-4-(2-hydroxyethylamino)benzene;
- 2-methoxymethyl-p-phenylenediamine/2-amino-3-hydroxypyridine;
- 2-methoxymethyl-p-phenylenediamine/1-naphthol;
- N-(4-amino-3-methylphenyl)-N-[3-(1H-imidazol-1-yl)propyl]amine/resorcinol;
- N-(4-amino-3-methylphenyl)-N-[3-(1H-imidazol-1-yl)propyl]amine/2-methylresorcinol;
- N-(4-amino-3-methylphenyl)-N-[3-(1H-imidazol-1-yl)propyl]amine/5-amino-2-methylphenol;
- N-(4-amino-3-methylphenyl)-N-[3-(1H-imidazol-1-yl)propyl]amine/3-aminophenol;
- N-(4-amino-3-methylphenyl)-N-[3-(1H-imidazol-1-yl)propyl]amine 2-(2,4-diaminophenoxy)ethanol;

N-(4-amino-3-methylphenyl)-N-[3-(1H-imidazol-1-yl)propyl]amine/1,3-bis-(2,4-diaminophenoxy)propane;
N-(4-amino-3-methylphenyl)-N-[3-(1H-imidazol-1-yl)propyl]amine/1-methoxy-2-amino-4-(2-hydroxyethylamino)benzene;
N-(4-amino-3-methylphenyl)-N-[3-(1H-imidazol-1-yl)propyl]amine/2-amino-3-hydroxypyridine;
N-(4-amino-3-methylphenyl)-N-[3-(1H-imidazol-1-yl)propyl]amine/1-naphthol;
4,5-diamino-1-(2-hydroxyethyl)pyrazole/resorcinol;
4,5-diamino-1-(2-hydroxyethyl)pyrazole/2-methylresorcinol;
4,5-diamino-1-(2-hydroxyethyl)pyrazole/5-amino-2-methylphenol;
4,5-diamino-1-(2-hydroxyethyl)pyrazole/3-aminophenol;
4,5-diamino-1-(2-hydroxyethyl)pyrazole/2-(2,4-diaminophenoxy)ethanol;
4,5-diamino-1-(2-hydroxyethyl)pyrazole/1,3-bis-(2,4-diaminophenoxy)propane;
4,5-diamino-1-(2-hydroxyethyl)pyrazole 1-methoxy-2-amino-4-(2-hydroxyethylamino)benzene;
4,5-diamino-1-(2-hydroxyethyl)pyrazole/2-amino-3-hydroxypyridine;
4,5-diamino-1-(2-hydroxyethyl)pyrazole/1-naphthol.

The combinations 4,5-diamino-1-(2-hydroxyethyl)pyrazole/3-aminophenol and p-toluoylenediamine/3-aminophenol are particularly preferred according to the present invention. The combination 4,5-diamino-1-(2-hydroxyethyl)pyrazole/3-aminophenol is extraordinarily preferred, in particular in terms of improving washing fastness.

In order to achieve balanced and subtle toning, it is preferred according to the present invention if further color-imparting components are contained in the coloring agent that is used in the method according to the present invention.

In a further embodiment, the agents used in step b) of this variant of the method according to the present invention can additionally contain at least one substantive dye. These are dyes that absorb directly onto the hair and do not require an oxidizing process for formation of the color. Substantive dyes are usually nitrophenylenediamines, nitroaminophenols, azo dyes, anthraquinones, or indophenols.

A further preferred method according to the present invention is characterized in that the coloring agent applied in step b) is rinsed off the fibers after a period from about 5 to about 60 minutes, preferably about 30 to about 45 minutes.

The coloring agent used in the method according to the present invention in step b) is produced from a two-component agent, where one component, namely composition (A), contains the oxidation dye precursors and the other component, namely composition (B), contains the oxidizing agent or agents. The ready-to-use coloring agent for step b) is then produced by mixing the two components directly before the application step b). A separation into multi-component systems is advisable in particular when incompatibilities of the ingredients are expected or are a concern.

EXEMPLIFYING EMBODIMENTS

Example 1

Hair skeins were immersed for one minute into an aqueous emulsion of a 4-morpholinomethyl-substituted silicone of formula (V) that contained 0.01 wt % 4-morpholinomethyl-substituted silicone(s) of formula (V) and 0.005 wt % branched Trideceth-5, furthermore 0.006 wt % glycerol, and water to 100 wt %, and then blow-dried.

A freshly prepared coloring cream/oxidizing agent mixture was then applied onto the skeins and allowed to act for 30 minutes. The coloring agent was then rinsed out with water. The skeins were blow-dried for the color measurements. The combing tests were performed on damp skeins.

TABLE 1

| Composition (A): color cream (quantities indicated in wt %) | |
|---|---|
| Toluene-2,5-Diamine Sulfate | 0.02 |
| 2-Amino-4-Hydroxyethylaminoanisole Sulfate (1-methoxy-2-amino-4-(2'-hydroxyethylamino)benzene sulfate) | 0.02 |
| 4-Amino-2-Hydroxytoluene | 0.01 |
| Cetearyl Alcohol | 14 |
| Glyceryl Stearate | 1.4 |
| Ammonium Hydroxide | 6.8 |
| Ceteareth-20 | 3.5 |
| Octyldodecanol | 1 |
| Sodium Laureth Sulfate | 0.5 |
| 1,3-Butylene glycol | 3.5 |
| Sodium Cetearyl Sulfate | 1.0 |
| Oleic Acid | 0.1 |
| Perfume (Fragrance) | 0.5 |
| Potassium Stearate | 0.5 |
| Sodium Sulfite | 0.2 |
| Tetrasodium EDTA | 0.3 |
| Carbomer | 0.3 |
| Polyquaternium-39 (ex Merquat 3330) | 0.05 |
| Potassium Hydroxide | 0.08 |
| Ascorbic Acid | 0.02 |
| Linoleamidopropyl PG-Dimonium Chloride Phosphate | 0.1 |
| Sodium Sulfate | 0.1 |
| Citric Acid | 0.002 |
| CI 77891 (Titanium Dioxide) | 0.3 |
| Aqua (Water, Eau) | to 100 |

The composition (A) listed above (=color cream 12-0) was mixed at a 1:1 weight ratio either with the composition (B)-E presented below (=Oxidizing agent composition (B) having an oil content according to the present invention), or with the composition (B)-V presented below (=Oxidizing agent composition (B) having a lower oil content), to yield a respective ready-to-use coloring agent. The ready-to-use coloring agent was then applied onto the test skeins, specifically at a rate of 4 g coloring agent per gram of hair. The test skeins used were on the one hand ones that had previously been treated with the 4-morpholinomethyl-substituted silicone of formula (V), and on the other hand untreated test skeins.

The coloring agent remained on the skeins for 30 minutes in each case. The skeins were then rinsed out for 2 minutes using warm (32° C.) tap water at a flow rate of 0.5 liter per minute.

TABLE 2

| Composition (B)-E used for the method according to the present invention (quantities indicated in wt %) | |
|---|---|
| Paraffinum Liquidum | 17.00 |
| Cetearyl Alcohol | 4.00 |
| Dipicolinic acid | 0.10 |
| Disodium Pyrophosphate | 0.10 |
| Potassium Hydroxide | 0.12 |
| Etidronic Acid | 0.20 |
| PEG-40 Castor Oil | 0.70 |
| Sodium Cetearyl Sulfate | 0.40 |
| $H_2O_2$ (active content) | 6.00 |
| Water | to100.00 |

TABLE 3

Composition (B)-V used for the comparison method (quantities indicated in wt %)

| | |
|---|---|
| Paraffinum Liquidum | 0.5 |
| Cetearyl Alcohol | 4.0 |
| Dipicolinic acid | 0.1 |
| Disodium Pyrophosphate | 0.1 |
| Potassium hydroxide | 0.1 |
| 1,2-Propylene glycol | 1.0 |
| 1-Hydroxyethane-1,1-Diphosphonic Acid (Etidronic Acid) | 0.1 |
| Steartrimonium Chloride | 0.5 |
| Ceteareth-20 | 1.0 |
| $H_2O_2$ (active content) | 12.0 |
| Water | to 100 |

TABLE 4

Wet combability; combing work (mJ)

| | Combing work (mJ) | Relative change (%) |
|---|---|---|
| (A) + (B)-V, without method step a) (comparison) | 1248 | 100 |
| (A) + (B)-E, without method step a) (comparison) | 905 | 73 |
| (A) + (B)-V, with method step a) (comparison) | 976 | 78 |
| (A) + (B)-E, with method step a) (according to the present invention) | 728 | 58 |

TABLE 5

Split count after 20,000 comb strokes (proportion as %)

| | Split count (%) | Relative change (%) |
|---|---|---|
| (A) + (B)-V, without method step a) (comparison) | 1.8 | 00 |
| (A) + (B)-E, without method step a) (comparison) | 1.3 | 72 |
| (A) + (B)-V, with method step a) (comparison) | 1.1 | 61 |
| (A) + (B)-E, with method step a) (according to the present invention) | 0.9 | 50 |

As shown by the data presented in Tables 4 and 5, both the pretreatment using a 4-morpholinomethyl-substituted silicone of formula (V) alone, and the use of an oxidizing agent composition (B) having a high oil content alone, already have a positive effect on protection of the hair from oxidative damage: not only is combing work reduced by 20 resp. 27% (lower combing work being equivalent to less hair damage), but the number of splits caused by standardized test combing is reduced by 28 resp. 39%.

In contrast, the method according to the present invention, which combines pretreatment with the 4-morpholinomethyl-substituted silicone of formula (V) with the use of an oxidizing agent composition (B) having a high oil content, brings a further very appreciable reduction in wet combing work and in the splitting rate.

The invention claimed is:

1. A method for oxidative coloring of keratinic fibers, in particular of hair, the method comprising the steps of:

applying a pretreatment agent onto the keratinic fibers, in particular onto the hair, wherein the pretreatment agent contains;

at least one 4-morpholinomethyl-substituted silicone of formula (V),

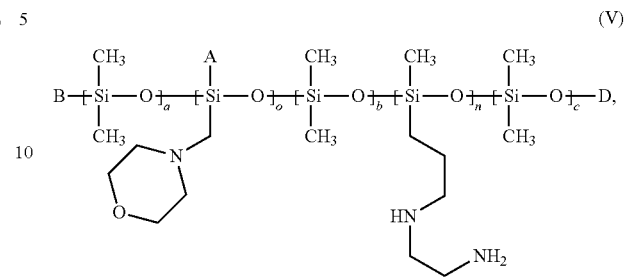

in which
A denotes a structural unit (I), (II), or (III) bound via —O

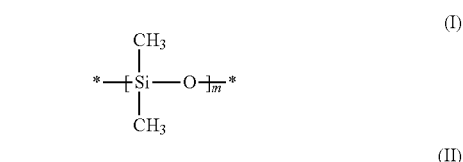

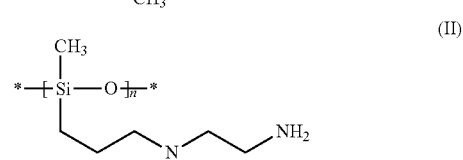

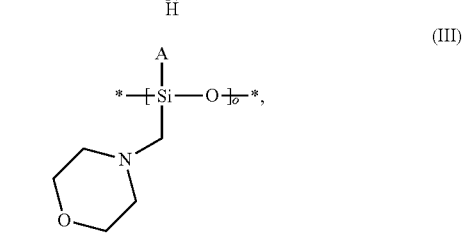

or an oligomeric or polymeric residue bound via —O— containing structural units of formulas (I), (II), or (III), or half of an oxygen atom connecting to a structural unit (III), or denotes —OH, denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers from 0 to 990, with the provision that a+b+c>0, m, n, and o denote integers from 1 to 990, applying a hair coloring agent onto the keratinic fibers subsequent to the pretreatment agent, and within a time span from about one second to about 24 hours after applying the pretreatment agent, wherein the hair coloring agent is obtained by mixing a composition (A), which contains at least one oxidation dye precursor of the developer type and at least one oxidation dye precursor of the coupler type, with a composition (B) that contains at least one oxidizing agent, and wherein composition (B) contains at least one cosmetic oil in a total quantity from about 10 to about 80 wt %, based on the weight of composition (B).

2. The method according to claim 1, wherein applying the pretreatment agent further comprises applying the pretreatment agent wherein the pretreatment agent contains the at least one 4-morpholinomethyl-substituted silicone of formula (V) in which
m>(n+o) resp. (a+b+c)>(n+o), preferably
m>8(n+o) resp. (a+b+c)>8(n+o), particularly preferably
m>25(n+o) resp. (a+b+c)>25(n+o), more preferably
m>77(n+o) resp. (a+b+c)>77(n+o), and in particular
m>200(n+o) resp. (a+b+c)>200(n+o).

3. The method according to claim 1, wherein applying the pretreatment agent further comprises applying the pretreatment agent wherein the pretreatment agent contains, based on its weight, the at least one 4-morpholinomethyl-substituted silicone in a total quantity from about 0.001 to about 5 wt %, based on the total weight of the pretreatment agent.

4. The method according to claim 1, wherein applying the pretreatment agent further comprises applying the pretreatment agent, wherein the pretreatment agent contains, based on its weight, the at least one 4-morpholinomethyl-substituted silicone of formula (V) that respectively comprises at least one of the structural units of formulas (I), (II), and (III), in a total quantity from about 0.001 to about 5 wt %, based on the total weight of the pretreatment agent.

5. The method according to claim 1, wherein applying the pretreatment agent further comprises applying the pretreatment agent wherein the pretreatment agent contains a hydroxy-terminated 4-morpholinomethyl-substituted silicone in which the molar ratio of hydroxy to alkoxy is in the range from about 0.2:1 to about 0.4:1.

6. The method according to claim 1, wherein applying the pretreatment agent further comprises applying the pretreatment agent wherein the weight-average molar mass of the at least one 4-morpholinomethyl-substituted silicone of formula (V) is in the range from about 2,000 to about 1,000,000 grams per mole.

7. The method according to claim 1, wherein applying the pretreatment agent further comprises applying the pretreatment agent wherein the at least one 4-morpholinomethyl-substituted silicone of formula (V) is present in the form of an oil-in-water emulsion in which the number-average size of the silicone particles in the emulsion is in the range from about 3 to about 500 nanometers.

8. The method according to claim 1, wherein applying a hair coloring agent onto the keratinic fibers further comprises applying a hair coloring agent onto the keratinic fibers wherein the at least one cosmetic oil that is contained in composition (B) in a total quantity from about 10 to about 80 wt %, based on the weight of composition (B), is selected from: paraffin oils, including $C_{18}$ to $C_{30}$ isoparaffins; benzoic acid esters of linear or branched $C_{8-22}$ alkanols; fatty alcohols having 6 to 30 carbon atoms, which are unsaturated or branched and saturated or branched and unsaturated; triglycerides of linear or branched, saturated or unsaturated, optionally hydroxylated $C_{8-30}$ fatty acids, in particular natural oils; dicarboxylic acid esters of linear or branched $C_2$ to $C_{10}$ alkanols; esters of linear or branched, saturated or unsaturated fatty alcohols having 2 to 30 carbon atoms with linear or branched, saturated or unsaturated fatty acids having 2 to 30 carbon atoms, which can be hydroxylated; addition products of 1 to 5 propylene oxide units with mono- or polyvalent $C_{8-22}$ alkanols; addition products of at least 6 ethylene oxide and/or propylene oxide units with mono- or polyvalent $C_{3-22}$ alkanols; $C_8$ to $C_{22}$ fatty alcohol esters of monovalent or polyvalent $C_2$ to $C_7$ hydroxycarboxylic acids; symmetrical, asymmetrical, or cyclic esters of carbonic acid with $C_{3-22}$ alkanols, $C_{3-22}$ alkanediols, or $C_{3-22}$ alkanetriols; esters of dimers of unsaturated $C_{12}$ to $C_{22}$ fatty acids (dimer fatty acids) with monovalent linear, branched, or cyclic $C_2$ to $C_{18}$ alkanols or with polyvalent linear or branched $C_2$ to $C_6$ alkanols; silicone oils; and mixtures of the aforementioned substances.

9. The method according to claim 1, wherein applying a hair coloring agent onto the keratinic fibers further comprises applying a hair coloring agent onto the keratinic fibers wherein composition (B) contains the at least one cosmetic oil in a total quantity from about 12 to about 70 wt %, based on the weight of composition (B).

10. The method according to claim 1, wherein applying a hair coloring agent onto the keratinic fibers further comprises applying a hair coloring agent onto the keratinic fibers wherein composition (B) contains:
about 1 to about 24 wt % hydrogen peroxide (calculated as 100% $H_2O_2$);
furthermore
at least one cosmetic oil in a total quantity from about 12 to about 70 wt %;
furthermore
at least one surfactant in a total quantity from about 0.1 to about 5 wt %; as well as
at least one linear saturated alkanol having 12 to 30 carbon atoms, in a total quantity from about 0.1 to about 10 wt %;
where all "wt %" indications refer to the weight of composition (B).

11. The method according to claim 1, wherein applying a hair coloring agent onto the keratinic fibers further comprises applying a hair coloring agent onto the keratinic fibers wherein the hair coloring agent contains the at least one cosmetic oil in a total quantity from about 5 to about 50 wt %, based on the total weight of the hair coloring agent.

12. The method according to claim 1 further comprising:
rinsing out the hair, drying the hair, or combinations of rinsing and drying the hair, wherein drying the hair further comprises drying the hair with a towel, allowing the hair to air-dry, blow drying the hair, drying the hair with a drying hood, or combinations thereof, wherein drying the hair further comprises drying the hair at a temperature of from about 20° C. to about 150° C., and wherein rinsing out the hair and/or drying the hair is performed from about 2 seconds to about 120 minutes after applying the pretreatment agent onto the hair.

13. The method according to claim 1 further comprising:
drying the hair, wherein drying the hair further comprises drying the hair with a towel, allowing the hair to air-dry, blow drying the hair, drying the hair with a drying hood, or combinations thereof, wherein drying the hair further comprises drying the hair at a temperature of from about 20° C. to about 150° C., wherein drying the hair is performed from about 2 seconds to about 120 minutes after applying the pretreatment agent onto the hair, and wherein drying the hair further comprises drying the hair without rinsing out the hair such that no rinsing out of the hair occurs between applying the pretreatment agent and the drying of the hair.

14. The method according to claim 1, wherein applying a hair coloring agent onto the keratinic fibers further comprises applying a hair coloring agent onto the keratinic fibers from about 30 seconds to about 20 minutes after applying the pretreatment agent onto the hair.

15. The method according claim 1, wherein applying a hair coloring agent onto the keratinic fibers further comprises applying a hair coloring agent onto the keratinic fibers wherein the combination of the at least one oxidation dye precursor of the developer type and the at least one oxidation dye precursor of the coupler type applied is selected from at least one of the following combinations, where the amine compounds and the nitrogen heterocycles can also be present in the form of their physiologically acceptable salts:
- p-toluoylenediamine/resorcinol;
- p-toluoylenediamine/2-methylresorcinol;
- p-toluoylenediamine/5-amino-2-methylphenol;
- p-toluoylenediamine/3-aminophenol;
- p-toluoylenediamine/2-(2,4-diaminophenoxy)ethanol;
- p-toluoylenediamine/1,3-bis(2,4-diaminophenoxy)propane;
- p-toluoylenediamine/1-methoxy-2-amino-4-(2-hydroxyethylamino)benzene;
- p-toluoylenediamine/2-amino-3-hydroxypyridine;
- p-toluoylenediamine/1-naphthol;
- 2-(2-hydroxyethyl)-p-phenylenediamine/resorcinol;
- 2-(2-hydroxyethyl)-p-phenylenediamine/2-methylresorcinol;
- 2-(2-hydroxyethyl)-p-phenylenediamine/5-amino-2-methylphenol;
- 2-(2-hydroxyethyl)-p-phenylenediamine/3-aminophenol;
- 2-(2-hydroxyethyl)-p-phenylenediamine/2-(2,4-diaminophenoxy)ethanol;
- 2-(2-hydroxyethyl)-p-phenylenediamine/1,3-bis(2,4-diaminophenoxy)propane;
- 2-(2-hydroxyethyl)-p-phenylenediamine/1-methoxy-2-amino-4-(2-hydroxyethylamino)benzene;
- 2-(2-hydroxyethyl)-p-phenylenediamine/2-amino-3-hydroxypyridine;
- 2-(2-hydroxyethyl)-p-phenylenediamine/1-naphthol;
- 2-methoxymethyl-p-phenylenediamine/resorcinol;
- 2-methoxymethyl-p-phenylenediamine/2-methylresorcinol;
- 2-methoxymethyl-p-phenylenediamine/5-amino-2-methylphenol;
- 2-methoxymethyl-p-phenylenediamine/3-aminophenol;
- 2-methoxymethyl-p-phenylenediamine/2-(2,4-diaminophenoxy)ethanol;
- 2-methoxymethyl-p-phenylenediamine/1,3-bis(2,4-diaminophenoxy)propane;
- 2-methoxymethyl-p-phenylenediamine/1-methoxy-2-amino-4-(2-hydroxyethylamino)benzene;
- 2-methoxymethyl-p-phenylenediamine/2-amino-3-hydroxypyridine;
- 2-methoxymethyl-p-phenylenediamine/1-naphthol;
- N-(4-amino-3-methylphenyl)-N-[3-(1H-imidazol-1-yl)propyl]amine/resorcinol;
- N-(4-amino-3-methylphenyl)-N-[3-(1H-imidazol-1-yl)propyl]amine 2-methylresorcinol;
- N-(4-amino-3-methylphenyl)-N-[3-(1H-imidazol-1-yl)propyl]amine/5-amino-2-methylphenol;
- N-(4-amino-3-methylphenyl)-N-[3-(1H-imidazol-1-yl)propyl]amine 3-aminophenol;
- N-(4-amino-3-methylphenyl)-N-[3-(1H-imidazol-1-yl)propyl]amine/2-(2,4-diaminophenoxy)ethanol;
- N-(4-amino-3-methylphenyl)-N-[3-(1H-imidazol-1-yl)propyl]amine/1,3-bis(2,4-diaminophenoxy)propane;
- N-(4-amino-3-methylphenyl)-N-[3-(1H-imidazol-1-yl)propyl]amine/1-methoxy-2-amino-4-(2-hydroxyethylamino)benzene;
- N-(4-amino-3-methylphenyl)-N-[3-(1H-imidazol-1-yl)propyl]amine/2-amino-3-hydroxypyridine;
- N-(4-amino-3-methylphenyl)-N-[3-(1H-imidazol-1-yl)propyl]amine/1-naphthol;
- 4,5-diamino-1-(2-hydroxyethyl)pyrazole/resorcinol;
- 4,5-diamino-1-(2-hydroxyethyl)pyrazole/2-methylresorcinol;
- 4,5-diamino-1-(2-hydroxyethyl)pyrazole/5-amino-2-methylphenol;
- 4,5-diamino-1-(2-hydroxyethyl)pyrazole/3-aminophenol;
- 4,5-diamino-1-(2-hydroxyethyl)pyrazole/2-(2,4-diaminophenoxy)ethanol;
- 4,5-diamino-1-(2-hydroxyethyl)pyrazole/1,3-bis(2,4-diaminophenoxy)propane;
- 4,5-diamino-1-(2-hydroxyethyl)pyrazole 1-methoxy-2-amino-4-(2-hydroxyethylamino)benzene;
- 4,5-diamino-1-(2-hydroxyethyl)pyrazole/2-amino-3-hydroxypyridine;
- 4,5-diamino-1-(2-hydroxyethyl)pyrazole/1-naphthol.

* * * * *